US008883155B2

(12) United States Patent
David et al.

(10) Patent No.: US 8,883,155 B2
(45) Date of Patent: Nov. 11, 2014

(54) METHODS FOR TREATING HEMATOPOIETIC MALIGNANCIES

(75) Inventors: Michael David, San Diego, CA (US); Irene Munk Pedersen, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 650 days.

(21) Appl. No.: 12/919,708

(22) PCT Filed: Jan. 22, 2009

(86) PCT No.: PCT/US2009/000412
§ 371 (c)(1),
(2), (4) Date: Feb. 2, 2011

(87) PCT Pub. No.: WO2009/097095
PCT Pub. Date: Aug. 6, 2009

(65) Prior Publication Data
US 2011/0123524 A1 May 26, 2011

Related U.S. Application Data

(60) Provisional application No. 61/062,725, filed on Jan. 28, 2008.

(51) Int. Cl.
*A61K 39/395* (2006.01)
*A61K 38/17* (2006.01)
*C07K 16/24* (2006.01)
*C07K 16/30* (2006.01)

(52) U.S. Cl.
CPC ....... *A61K 38/1793* (2013.01); *A61K 39/39558* (2013.01); *C07K 16/241* (2013.01); *C07K 16/3061* (2013.01)
USPC ...................................................... 424/145.1

(58) Field of Classification Search
None
See application file for complete search history.

(56) References Cited

U.S. PATENT DOCUMENTS

| | | | |
|---|---|---|---|
| 5,223,395 A | 6/1993 | Gero | 435/7.1 |
| 5,654,407 A | 8/1997 | Boyle | 530/388.15 |
| 5,672,347 A | 9/1997 | Aggarwal | 424/139.1 |
| 5,736,137 A | 4/1998 | Anderson | 424/133.1 |
| 5,795,967 A | 8/1998 | Aggarwal | 530/388.23 |
| 6,379,666 B1 | 4/2002 | Tobinick | 424/134.1 |
| 6,419,944 B2 | 7/2002 | Tobinick | 424/422 |
| 6,537,549 B2 | 3/2003 | Tobinick | 424/134.1 |
| 6,649,589 B1 | 11/2003 | Olmarker | 514/2 |
| 6,982,089 B2 | 1/2006 | Tobinick | 424/400 |
| 7,244,450 B2 | 7/2007 | Sarris | 424/450 |
| 7,252,823 B2 | 8/2007 | Le | 424/133.1 |

OTHER PUBLICATIONS

Kluiver et al., Oncogene (2007) 26, 3769-3776.*
Francis et al., Int Immunol. Feb. 1995;7(2):151-61.*
Adams et al., J Am Acad Dermatol 2004;51:660-2.*
Rube et al., Int. J. Radiation Oncology Biol. Phys., vol. 56, No. 5, pp. 1414-1425, 2003.*
Fey, Ann Oncol. Jan. 2007;18 Suppl 1:i54-i64.*
Robert Weinberg, the Biology of Cancer, Garland Press, 2007, pp. 536-539 and Sidebar 25.*
Graeber et al., Nature Genetics • vol. 29 • Nov. 2001, pp. 295-300.*
Alizadeh, A. A. et al. (2000) "Distinct types of diffuse large B-cell lymphoma identified by gene expression profiling," *Nature* 403(6769), 503-511.
Better, M. et al. (1988) "*Escherichia coli* Secretion of an Active Chimeric Antibody Fragment," *Science* 240(4855), 1041-1043.
Bouliaune, G. L. et al. (1984) "Production of functional chimaeric mouse/human antibody," *Nature* 312(5995), 643-646.
Cabilly, S. et al. (1984) "Generation of antibody activity from immunoglobulin polypeptide chains produced in *Escherichia coli*," *P.N.A.S.* 81(11), 3273-3277.
Calin, G. A. et al. (2006) "MicroRNA signatures in human cancers," *Nat. Rev. Cancer* 6(11), 857-866.
Calin, G. A. et al. (2002) "Frequent deletions and down-regulation of micro-RNA genes miR15 and miR16 at 13q14 in chronic lymphocytic leukemia," *P.N.A.S.* 99(24), 15524-15529.
Calin, G. A. et al. (2004) "Human microRNA genes are frequently located at fragile sites and genomic regions involved in cancers," *Proc. Natl. Acad. Sci. U. S. A.* 101(9), 2999-3004.
Cimmino, A. et al. (2005) "miR-15 and miR-16 induce apoptosis by targeting BCL2," *Proc. Natl. Acad. Sci. U. S. A.* 102(39), 13944-13949.
Costinean, S. et al. (2006) "Pre-B cell proliferation and lymphoblastic leukemia/high-grade lymphoma in Eμ-miR155 transgenic mice," *P.N.A.S.* 103(18), 7024-7029.
Eis, P. S. et al. (2005) "Accumulation of miR-155 and BIC RNA in human B cell lymphomas," *Proc. Natl. Acad. Sci. U. S. A.* 102(10), 3627-3632.
Esquela-Kerscher, A. et al. (2006) "Oncomirs [mdash] microRNAs with a role in cancer," *Nat. Rev. Cancer* 6(4), 259-269.
Furman, D. A. (2004) "Phosphoinositide 3-kinase and its targets in B-cell and T-cell signaling," *Curr. Opin. Immunol.* 16(3), 314-320.
Habermann, T. M. et al. (2006) "Rituximab-CHOP Versus CHOP Alone or With Maintenance Rituximab in Older Patients With Diffuse Large B-Cell Lymphoma," J. Clin. Oncol. 24(19), 3121-3127.
He, L. et al. (2005) "A microRNA polycistron as a potential human oncogene," Nature 435(7043), 828-833.
Johnson, S. M. et al. (2005) "RAS Is Regulated by the let-7 MicroRNA Family," Cell 120(5), 635-647.
Köhler, G. et al. (1975) "Continuous cultures of fused cells secreting antibody of predefined specificity," *Nature* 256(5517), 495-497.

(Continued)

*Primary Examiner* — Zachary Skelding
(74) *Attorney, Agent, or Firm* — Medlen & Carroll, LLP

(57) ABSTRACT

The present invention relates to methods for treating neoplasias in a mammalian subject. In particular, the invention provides methods for treating lymphomas, including forms of non-Hodgkin lymphoma. In one embodiment, these methods involve reducing tumor necrosis factor signaling.

5 Claims, 26 Drawing Sheets

(56) References Cited

OTHER PUBLICATIONS

Lawrie, C. H. (2007) "MicroRNAs and haematology: small molecules, big function," *Br. J. Haematol.* 137(6), 503-512.

Lawrie, C. H. et al. (2007) "Microrna expression distinguishes between germinal center B cell-like and activated B cell-like subtypes of diffuse large B cell lymphoma," *Int. J. Cancer* 121(5), 1156-1161.

Liu, A. Y. et al. (1987) "Chimeric mouse-human IgG1 antibody that can mediate lysis of cancer cells," *P.N.A.S.* 84(10), 3439-3443.

Lu, J. et al. (2005) "MicroRNA expression profiles classify human cancers," *Nature* 435(7043), 834-838.

Ma, L. et al. (2007) "Tumour invasion and metastasis initiated by microRNA-10b in breast cancer," *Nature* 449(7163), 682-688.

Morrison, S. L. et al. (1984) "Chimeric human antibody molecules: mouse antigen-binding domains with human constant region domains," *P.N.A.S.* 81(21), 6851-6855.

Neuberger, M. S. et al. (1985) "A hapten-specific chimaeric IgE antibody with human physiological effector function," *Nature* 314(6008), 268-270.

O'Connell, R. M. et al. (2007) "MicroRNA-155 is induced during the macrophage inflammatory response," *P.N.A.S.* 104(5), 1604-1609.

O'Donnell, K. A. et al. (2005) "c-Myc-regulated microRNAs modulate E2F1 expression," *Nature* 435(7043), 839-843.

Ota, A. et al. (2004) "Identification and Characterization of a Novel Gene, C13orf25, as a Target for 13q31-q32 Amplification in Malignant Lymphoma," *Cancer Res.* 64(9), 3087-3095.

Pedersen, L. M. et al. (2005) "Serum levels of inflammatory cytokines at diagnosis correlate to the bcl-6 and CD10 defined germinal centre (GC) phenotype and bcl-2 expression in patients with diffuse large B-cell lymphoma," *Br. J. Haematol.* 128(6), 813-819.

Pfreundschuh, M. et al. (2008) "Prognostic significance of maximum tumour (bulk) diameter in young patients with good-prognosis diffuse large-B-cell lymphoma treated with CHOP-like chemotherapy with or without rituximab: an exploratory analysis of the MabThera International Trial Group (MInT) study," *The Lancet Oncology* 9(5), 435-444.

Pitot, H. C. (1978) "The Language of Oncology," in *Fundamentals of Oncology* (Dekker, M., Ed.), pp. 15-28, New York.

Project, T. N.-H. s. L. C. (1997) "A Clinical Evaluation of the International Lymphoma Study Group Classification of Non-Hodgkin's Lymphoma," *Blood* 89(11), 3909-3918.

Rhodes, D. R. et al. (2005) "Mining for regulatory programs in the cancer transcriptome," *Nat. Genet.* 37(6), 579-583.

Rhodes, D. R. et al. (2007) "Oncomine 3.0: genes, pathways, and networks in a collection of 18,000 cancer gene expression profiles," *Neoplasia* 9(2), 166-180.

Rhodes, D. R. et al. (2004) "ONCOMINE: a cancer microarray database and integrated data-mining platform," *Neoplasia* 6(1), 1-6.

Rhodes, D. R. et al. (2004) "Large-scale meta-analysis of cancer microarray data identifies common transcriptional profiles of neoplastic transformation and progression," *Proc. Natl. Acad. Sci. U. S. A.* 101(25), 9309-9314.

Roldo, C. et al. (2006) "MicroRNA Expression Abnormalities in Pancreatic Endocrine and Acinar Tumors Are Associated With Distinctive Pathologic Features and Clinical Behavior," *J. Clin. Oncol.* 24(29), 4677-4684.

Rosenwald, A. et al. (2002) "The Use of Molecular Profiling to Predict Survival after Chemotherapy for Diffuse Large-B-Cell Lymphoma," *N. Engl. J. Med.* 346(25), 1937-1947.

Rosenwald, A. et al. (2003) "Molecular Diagnosis of Primary Mediastinal B Cell Lymphoma Identifies a Clinically Favorable Subgroup of Diffuse Large B Cell Lymphoma Related to Hodgkin Lymphoma," *J. Exp. Med.* 198(6), 851-862.

Sahagan, B. G. et al. (1986) "A genetically engineered murine/human chimeric antibody retains specificity for human tumor-associated antigen," *J. Immunol.* 137(3), 1066-1074.

Shipp, M. A. et al. (2002) "Diffuse large B-cell lymphoma outcome prediction by gene-expression profiling and supervised machine learning," *Nat. Med.* 8(1), 68-74.

Sun, L. K. et al. (1987) "Chimeric antibody with human constant regions and mouse variable regions directed against carcinoma-associated antigen 17-1A," *P.N.A.S.* 84(1), 214-218.

\* cited by examiner

Predicted Pairing of Target and miRNA

```
SHIP    5' ...GUGUUC - GGAGGGGUGAAAGCAUUAA...    SEQ ID NO: 1
              : :|      :  |:|   |||||||
miR-155 3'     GGGGAUAGUGCUA - - AUCGUAAUU       SEQ ID NO: 2
```

Figure 3

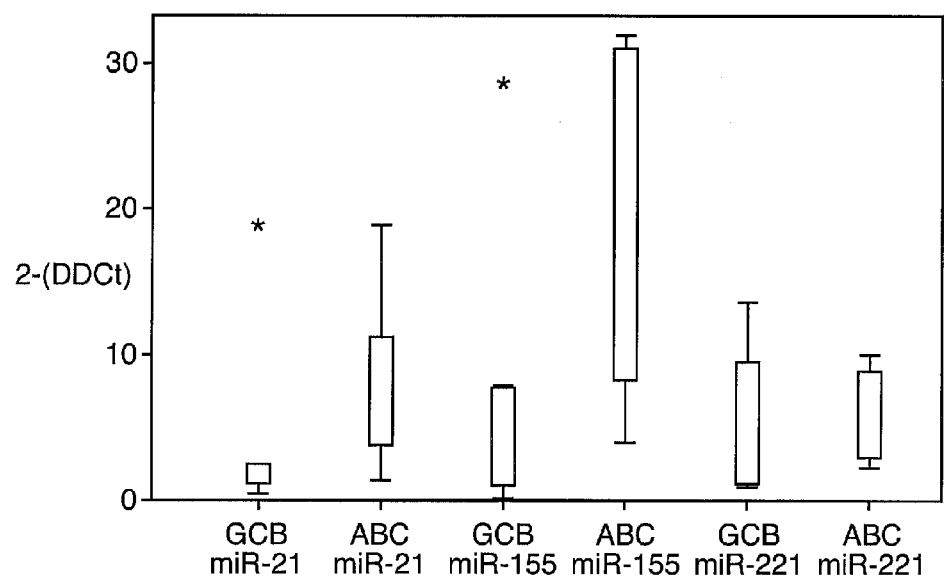
FIG. 7A
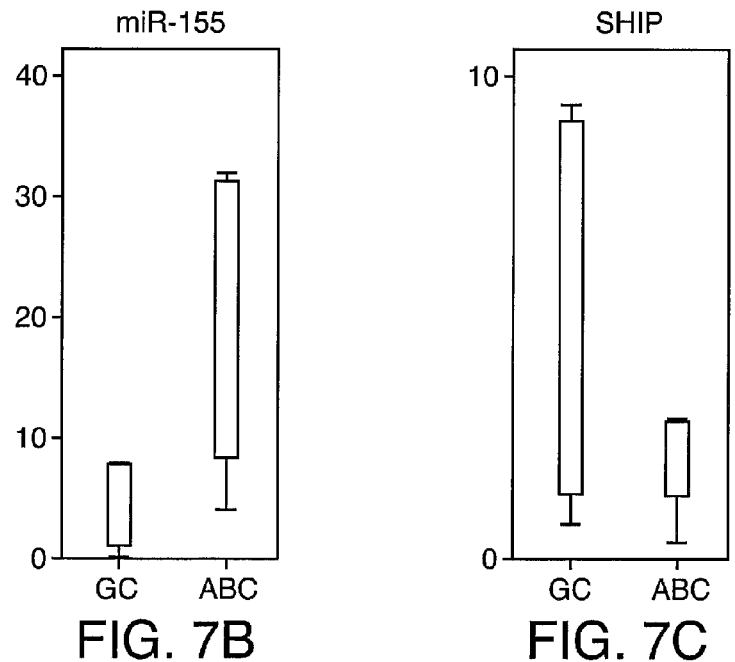
FIG. 7B
FIG. 7C

Figure 9
A.
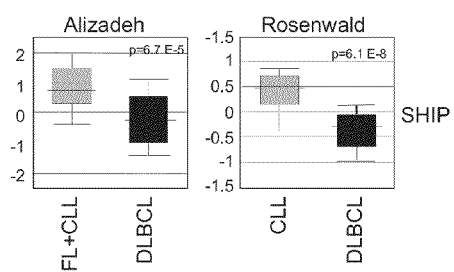
B.
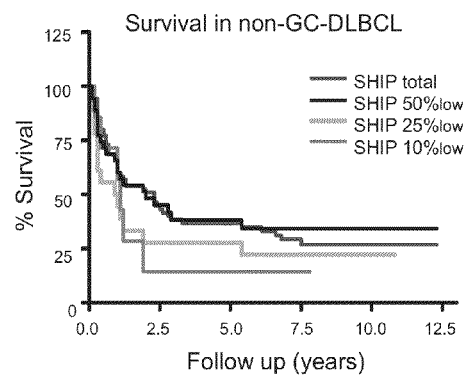
C.
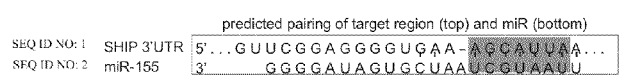
D.
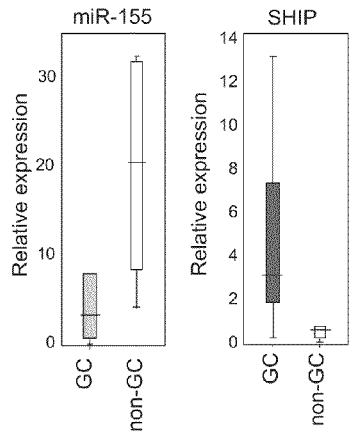

MSTESMIRDVELAEEALPKKTGGPQGSRRCLFLSLFSFLIVAGA
TTLFCLLHFGVIGPQREEFPRDLSLISPLAQAVRSSSRTPSDKPVAHVVANPQAEGQL
QWLNRRANALLANGVELRDNQLVVPSEGLYLIYSQVLFKGQGCPSTHVLLTHTISRIA
VSYQTKVNLLSAIKSPCQRETPEGAEAKPWYEPIYLGGVFQLEKGDRLSAEINRPDYL
DFAESGQVYFGIIAL

```
  1 ctccctcagc aaggacagca gaggaccagc taagagggag agaagcaact acagaccccc
 61 cctgaaaaca accctcagac gccacatccc ctgacaagct gccaggcagg ttctcttcct
121 ctcacatact gacccacggc tccaccctct ctccctgga aaggacacca tgagcactga
181 aagcatgatc cgggacgtgg agctggccga ggaggcgctc cccaagaaga caggggggcc
241 ccagggctcc aggcggtgct tgttcctcag cctcttctcc ttcctgatcg tggcaggcgc
301 caccacgctc ttctgcctgc tgcactttgg agtgatcggc cccagaggg aagagttccc
361 cagggacctc tctctaatca gccctctggc ccaggcagtc agatcatctt ctcgaacccc
421 gagtgacaag cctgtagccc atgttgtagc aaaccctcaa gctgaggggc agctccagtg
481 gctgaaccgc cgggccaatg ccctcctggc caatggcgtg gagctgagag ataaccagct
541 ggtggtgcca tcagagggcc tgtacctcat ctactcccag gtcctcttca gggccaagg
601 ctgccctcc acccatgtgc tcctcaccca caccatcagc cgcatcgccg tctcctacca
661 gaccaaggtc aacctcctct ctgccatcaa gagccctgc cagagggaga ccccagaggg
721 ggctgaggcc aagccctggt atgagcccat ctatctggga ggggtcttcc agctggagaa
```

FIG 13A 781 gggtgaccga ctcagcgctg agatcaatcg gcccgactat ctcgactttg ccgagtctgg 841 gcaggtctac tttgggatca ttgccctgtg aggaggacga acatccaacc ttcccaaacg 901 cctccctgc cccaatccct ttattacccc ctccttcaga caccctcaac ctcttctggc 961 tcaaaaagag aattgggggc ttagggtcgg aacccaagct tagaacttta agcaacaaga 1021 ccaccacttc gaaacctggg attcaggaat gtgtggcctg cacagtgaag tgctggcaac 1081 cactaagaat tcaaactggg gcctccagaa ctcactgggg cctacagctt tgatccctga 1141 catctggaat ctggagacca gggagccttt ggttctggcc agaatgctgc aggacttgag 1201 aagacctcac ctagaaattg acacaagtgg accttaggcc ttcctctctc cagatgtttc 1261 cagacttcct tgagacacgg agcccagccc tccccatgga gccagctccc tctatttatg 1321 tttgcacttg tgattattta ttatttattt attatttatt tatttacaga tgaatgtatt 1381 tatttgggag accggggtat cctgggggac ccaatgtagg agctgccttg gctcagacat 1441 gttttccgtg aaaacggagc tgaacaatag gctgttccca tgtagccccc tggcctctgt 1501 gccttctttt gattatgttt tttaaaatat ttatctgatt aagttgtcta aacaatgctg 1561 atttggtgac caactgtcac tcattgctga gcctctgctc cccaggggag ttgtgtctgt 1621 aatcgcccta ctattcagtg gcgagaaata aagtttgctt agaaaagaa

FIG 13B

MTAIIKEIVSRNKRRYQEDGFDLDLTYIYPNIIAMGFPAERLEG

VYRNNIDDVVRFLDSKHKNHYKIYNLCAERHYDTAKFNCRVAQYPFEDHNPPQLELIK

PFCEDLDQWLSEDDNHVAAIHCKAGKGRTGVMICAYLLHRGKFLKAQEALDFYGEVRT

RDKKGVTIPSQRRYVYYYSYLLKNHLDYRPVALLFHKMMFETIPMFSGGTCNPQFVVC

QLKVKIYSSNSGPTRREDKFMYFEFPQPLPVCGDIKVEFFHKQNKMLKKDKMFHFWVN

TFFIPGPEETSEKVENGSLCDQEIDSICSIERADNDKEYLVLTLTKNDLDKANKDKAN

RYFSPNFKVKLYFTKTVEEPSNPEASSSTSVTPDVSDNEPDHYRYSDTTDSDPENEPF

DEDQHTQITKV

```
  1 cctccctcg ccggcgcgg tcccgtccgc ctctcgctcg cctcccgcct cccctcggtc
 61 ttccgaggcg cccgggctcc cggcgcggcg gcggaggggg cggccaggcc ggcgggcggt
121 gatgtggcgg gactctttat gcgctgcggc aggatacgcg ctcggcgctg ggacgcgact
181 gcgctcagtt ctctcctctc ggaagctgca gccatgatgg aagtttgaga gttgagccgc
241 tgtgaggcga ggccgggctc aggcgaggga gatgagagac ggcggcggcc gcggcccgga
301 gccctctca gcgcctgtga gcagccgcgg gggcagcgcc ctcggggagc cggccggcct
361 gcggcggcgg cagcggcggc gtttctcgcc tcctcttcgt cttttctaac cgtgcagcct
421 cttcctcggc ttctcctgaa agggaaggtg gaagccgtgg gctcgggcgg gagccggctg
481 aggcgcggcg gcggcggcg cacctcccgc tcctggagcg gggggagaa gcggcggcgg
541 cggcggccgc ggcggctgca gctccaggga ggggtctga gtcgcctgtc accatttcca
601 gggctgggaa cgccggagag ttggtctctc ccttctact gctccaaca cggcggcggc
661 gcggcggca catccaggga cccgggccgg ttttaaacct cccgtccgcc gccgccgcac
```

FIG 14A

721 cccccgtggc ccgggctccg gaggccgccg gcggaggcag ccgttcggag gattattcgt 781 cttctcccca ttccgctgcc gccgctgcca ggcctctggc tgctgaggag aagcaggccc 841 agtcgctgca accatccagc agccgccgca gcagccatta cccggctgcg gtccagagcc 901 aagcggcggc agagcgaggg gcatcagcta ccgccaagtc cagagccatt tccatcctgc 961 agaagaagcc ccgccaccag cagcttctgc catctctctc ctcctttttc ttcagccaca 1021 ggctcccaga catgacagcc atcatcaaag agatcgttag cagaaacaaa aggagatatc 1081 aagaggatgg attcgactta gacttgacct atatttatcc aaacattatt gctatgggat 1141 ttcctgcaga aagacttgaa ggcgtataca ggaacaatat tgatgatgta gtaaggtttt 1201 tggattcaaa gcataaaaac cattacaaga tatacaatct ttgtgctgaa agacattatg 1261 acaccgccaa atttaattgc agagttgcac aatatccttt tgaagaccat aacccaccac 1321 agctagaact tatcaaaccc ttttgtgaag atcttgacca atggctaagt gaagatgaca 1381 atcatgttgc agcaattcac tgtaaagctg aaagggacg aactggtgta atgatatgtg 1441 catatttatt acatcggggc aaattttaa aggcacaaga ggccctagat ttctatgggg 1501 aagtaaggac cagagacaaa aagggagtaa ctattcccag tcagaggcgc tatgtgtatt 1561 attatagcta cctgttaaag aatcatctgg attatagacc agtggcactg ttgtttcaca 1621 agatgatgtt tgaaactatt ccaatgttca gtggcggaac ttgcaatcct cagtttgtgg 1681 tctgccagct aaaggtgaag atatattcct ccaattcagg acccacacga cgggaagaca 1741 agttcatgta ctttgagttc cctcagccgt tacctgtgtg tggtgatatc aaagtagagt 1801 tcttccacaa acagaacaag atgctaaaaa aggacaaaat gtttcacttt tgggtaaata

FIG 14B

1861 cattcttcat accaggacca gaggaaacct cagaaaaagt agaaaatgga agtctatgtg 1921 atcaagaaat cgatagcatt tgcagtatag agcgtgcaga taatgacaag gaatatctag 1981 tacttacttt aacaaaaaat gatcttgaca aagcaaataa agacaaagcc aaccgatact 2041 tttctccaaa ttttaaggtg aagctgtact tcacaaaaac agtagaggag ccgtcaaatc 2101 cagaggctag cagttcaact tctgtaacac cagatgttag tgacaatgaa cctgatcatt 2161 atagatattc tgacaccact gactctgatc cagagaatga acctttgat gaagatcagc 2221 atacacaaat tacaaaagtc tgaatttttt tttatcaaga gggataaaac accatgaaaa 2281 taaacttgaa taaactgaaa atggaccttt ttttttttaa tggcaatagg acattgtgtc 2341 agattaccag ttataggaac aattctcttt tcctgaccaa tctgtttta ccctatacat 2401 ccacagggtt ttgacactg ttgtccagtt gaaaaaaggt tgtgtagctg tgtcatgtat 2461 ataccttttt gtgtcaaaag gacatttaaa attcaattag gattaataaa gatggcactt 2521 tcccgtttta ttccagtttt ataaaaagtg gagacagact gatgtgtata cgtaggaatt 2581 ttttcctttt gtgttctgtc accaactgaa gtggctaaag agctttgtga tatactggtt 2641 cacatcctac cccttttgcac ttgtggcaac agataagttt gcagttggct aagagaggtt 2701 tccgaagggt tttgctacat tctaatgcat gtattcgggt taggggaatg gagggaatgc 2761 tcagaaagga aataaatttta tgctggactc tggaccatat accatctcca gctatttaca 2821 cacacctttc tttagcatgc tacagttatt aatctggaca ttcgaggaat tggccgctgt 2881 cactgcttgt tgtttgcgca ttttttttta aagcatattg gtgctagaaa aggcagctaa 2941 aggaagtgaa tctgtattgg ggtacaggaa tgaaccttct gcaacatctt aagatccaca

FIG 14C 3001 aatgaaggga tataaaaata atgtcatagg taagaaacac agcaacaatg acttaaccat 3061 ataaatgtgg aggctatcaa caaagaatgg gcttgaaaca ttataaaaat tgacaatgat 3121 ttattaaata tgttttctca attgtaacga cttctccatc tcctgtgtaa tcaaggccag 3181 tgctaaaatt cagatgctgt tagtacctac atcagtcaac aacttacact tatttacta 3241 gttttcaatc ataatacctg ctgtggatgc ttcatgtgct gcctgcaagc ttctttttc 3301 tcattaaata taaatattt tgtaatgctg cacagaaatt ttcaatttga gattctacag 3361 taagcgtttt ttttctttga agatttatga tgcacttatt caatagctgt cagccgttcc 3421 acccttttga ccttacacat tctattacaa tgaattttgc agttttgcac attttttaaa 3481 tgtcattaac tgttagggaa tttacttga atactgaata catataatgt tatattaaa 3541 aaggacattt gtgttaaaaa ggaaattaga gttgcagtaa actttcaatg ctgcacacaa 3601 aaaaaagaca tttgattttt cagtagaaat tgtcctacat gtgctttatt gatttgctat 3661 tgaaagaata gggtttttt tttttttt tttttttt ttaaatgtgc agtgttgaat 3721 catttcttca tagtgctccc ccgagttggg actagggctt caatttcact tcttaaaaaa 3781 aatcatcata tatttgatat gcccagactg catacgattt taagcggagt acaactacta 3841 ttgtaaagct aatgtgaaga tattataaa aaggttttt ttccagaaa tttggtgtct 3901 tcaaattata ccttcaccttt gacatttgaa tatccagcca ttttgtttct taatggtata 3961 aaattccatt ttcaataact tattggtgct gaaattgttc actagctgtg gtctgaccta 4021 gttaatttac aaatacagat tgaataggac ctactagagc agcatttata gagtttgatg 4081 gcaaatagat taggcagaac ttcatctaaa atattcttag taaataatgt tgacacgttt

FIG 14D 4141 tccataccttt gtcagtttca ttcaacaatt tttaaatttt taacaaagct cttaggattt 4201 acacatttat atttaaacat tgatatatag agtattgatt gattgctcat aagttaaatt 4261 ggtaaagtta gagacaacta ttctaacacc tcaccattga aatttatatg ccaccttgtc 4321 tttcataaaa gctgaaaatt gttacctaaa atgaaaatca acttcatgtt ttgaagatag 4381 ttataaatat tgttctttgt tacaatttcg ggcaccgcat attaaaacgt aactttattg 4441 ttccaatatg taacatggag ggccaggtca taaataatga cattataatg ggcttttgca 4501 ctgttattat ttttcctttg gaatgtgaag gtctgaatga gggttttgat tttgaatgtt 4561 tcaatgtttt tgagaagcct tgcttacatt ttatggtgta gtcattggaa atggaaaaat 4621 ggcattatat atattatata tataaatata tattatacat actctcctta cttttatttca 4681 gttaccatcc ccatagaatt tgacaagaat tgctatgact gaaaggtttt cgagtcctaa 4741 ttaaaacttt atttatggca gtattcataa ttagcctgaa atgcattctg taggtaatct 4801 ctgagtttct ggaatatttt cttagacttt ttggatgtgc agcagcttac atgtctgaag 4861 ttacttgaag gcatcacttt taagaaagct tacagttggg ccctgtacca tcccaagtcc 4921 tttgtagctc ctcttgaaca tgtttgccat acttttaaaa gggtagttga ataaatagca 4981 tcaccattct ttgctgtggc acaggttata aacttaagtg gagtttaccg gcagcatcaa 5041 atgtttcagc tttaaaaaat aaaagtaggg tacaagttta atgtttagtt ctagaaattt 5101 tgtgcaatat gttcataacg atggctgtgg ttgccacaaa gtgcctcgtt tacctttaaa 5161 tactgttaat gtgtcatgca tgcagatgga aggggtggaa ctgtgcacta aagtggggc 5221 tttaactgta gtatttggca gagttgcctt ctacctgcca gttcaaaagt tcaacctgtt 5281 ttcatataga atatatatac taaaaaattt cagtctgtta aacagcctta ctctgattca

FIG 14E

5341 gcctcttcag atactcttgt gctgtgcagc agtggctctg tgtgtaaatg ctatgcactg 5401 aggatacaca aaaataccaa tatgatgtgt acaggataat gcctcatccc aatcagatgt 5461 ccatttgtta ttgtgtttgt taacaaccct ttatctctta gtgttataaa ctccacttaa 5521 aactgattaa agtctcattc ttgtcaaaaa aaaaaaaaaa aaaaaaaaaa aa

FIG 14F

MVPCWNHGNITRSKAEELLSRTGKDGSFLVRASESISRAYALCV

LYRNCVYTYRILPNEDDKFTVQASEGVSMRFFTKLDQLIEFYKKENMGLVTHLQYPVP

LEEEDTGDDPEEDTESVVSPPELPPRNIPLTASSCEAKEVPFSNENPRATETSRPSLS

ETLFQRLQSMDTSGLPEEHLKAIQDYLSTQLAQDSEFVKTGSSSLPHLKKLTTLLCKE

LYGEVIRTLPSLESLQRLFDQQLSPGLRPRPQVPGEANPINMVSKLSQLTSLLSSIED

KVKALLHEGPESPHRFSLIPPVTFEVKAESLGIPQKMQLKVDVESGKLIIKKSKDGSE

DKFYSHKKILQLIKSQKFLNKLVILVETEKEKILRKEYVFADSKKREGFCQLLQQMKN

KHSEQPEPDMITIFIGTWNMGNAPPPKKITSWFLSKGQGKTRDDSADYIPHDIYVIGT

QEDPLSEKEWLEILKHSLQEITSVTFKTVAIHTLWNIRIVVLAKPEHENRISHICTDN

VKTGIANTLGNKGAVGVSFMFNGTSLGFVNSHLTSGSEKKLRRNQNYMNILRFLALGD

KKLSPFNITHRFTHLFWFGDLNYRVDLPTWEAETIIQKIKQQQYADLLSHDQLLTERR

EQKVFLHFEEEEITFAPTYRFERLTRDKYAYTKQKATGMKYNLPSWCDRVLWKSYPLV

HVVCQSYGSTSDIMTSDHSPVFATFEAGVTSQFVSKNGPGTVDSQGQIEFLRCYATLK

TKSQTKFYLEFHSSCLESFVKSQEGENEEGSEGELVVKFGETLPKLKPIISDPEYLLD

QHILISIKSSDSDESYGEGCIALRLEATETQLPIYTPLTHHGELTGHFQGEIKLQTSQ

GKTREKLYDFVKTERDESSGPKTLKSLTSHDPMKQWEVTSRAPPCSGSSITEIINPNY

MGVGPFGPPMPLHVKQTLSPDQQPTAWSYDQPPKDSPLGPCRGESPPTPPGQPPISPK

KFLPSTANRGLPPRTQESRPSDLGKNAGDTLPQEDLPLTKPEMFENPLYGSLSSFPKP

APRKDQESPKMPRKEPPPCPEPGILSPSIVLTKAQEADRGEGPGKQVPAPRLRSFTCS

SSAEGRAAGGDKSQGKPKTPVSSQAPVPAKRPIKPSRSEINQQTPPTPTPRPPLPVKS

FIG 15A

PAVLHLQHSKGRDYRDNTELPHHGKHRPEEGPPGPLGRTAMQ

```
   1 tcggtggtgt gtgggtcctg ggggtgcctg ccggcccggc cgaggaggcc cacgcccacc
  61 atggtcccct gctggaacca tggcaacatc acccgctcca aggcggagga gctgctttcc
 121 aggacaggca aggacgggag cttcctcgtg cgtgccagcg agtccatctc ccgggcatac
 181 gcgctctgcg tgctgtatcg gaattgcgtt tacacttaca gaattctgcc caatgaagat
 241 gataaattca ctgttcaggc atccgaaggc gtctccatga ggttcttcac caagctggac
 301 cagctcatcg agttttacaa gaaggaaaac atggggctgg tgacccatct gcaataccct
 361 gtgccgctgg aggaagagga cacaggcgac gaccctgagg aggacacaga aagtgtcgtg
 421 tctccacccg agctgccccc aagaaacatc ccgctgactg ccagctcctg tgaggccaag
 481 gaggttcctt tttcaaacga gaatccccga gcgaccgaga ccagccggcc gagcctctcc
 541 gagacattgt tccagcgact gcaaagcatg gacaccagtg ggcttccaga gagcatctt
 601 aaggccatcc aagattattt aagcactcag ctcgcccagg actctgaatt tgtgaagaca
 661 gggtccagca gtcttcctca cctgaagaaa ctgaccacac tgctctgcaa ggagctctat
 721 ggagaagtca tccggaccct cccatccctg gagtctctgc agaggttatt tgaccagcag
 781 ctctccccgg gcctccgtcc acgtcctcag gttcctggtg aggccaatcc catcaacatg
 841 gtgtccaagc tcagccaact gacaagcctg ttgtcgtcca ttgaagacaa ggtcaaggcc
 901 ttgctgcacg agggtcctga gtctccgcac cggccctccc ttatccctcc agtcaccttt
 961 gaggtgaagg cagagtctct ggggattcct cagaaaatgc agctcaaagt cgacgttgag
1021 tctgggaaac tgatcattaa gaagtccaag gatggttctg aggacaagtt ctacagccac
```

FIG 15B

1081 aagaaaatcc tgcagctgat taagtcacag aaatttctga ataagttggt gatcttggtg 1141 gaaacagaga aggagaagat cctgcggaag gaatatgttt ttgctgactc caaaaagaga 1201 gaaggcttct gccagctcct gcagcagatg aagaacaagc actcagagca gccggagccc 1261 gacatgatca ccatcttcat cggcacctgg aacatgggta acgcccccc tcccaagaag 1321 atcacgtcct ggtttctctc caaggggcag ggaaagacgc gggacgactc tgcggactac 1381 atccccatg acatttacgt gatcggcacc caagaggacc ccctgagtga aaggagtgg 1441 ctggagatcc tcaaacactc cctgcaagaa atcaccagtg tgactttaa aacagtcgcc 1501 atccacacgc tctggaacat ccgcatcgtg gtgctggcca agcctgagca cgagaaccgg 1561 atcagccaca tctgtactga caacgtgaag acaggcattg caaacacact ggggaacaag 1621 ggagccgtgg gggtgtcgtt catgttcaat ggaacctcct tagggttcgt caacagccac 1681 ttgacttcag gaagtgaaaa gaaactcagg cgaaaccaaa actatatgaa cattctccgg 1741 ttcctggccc tgggcgacaa gaagctgagt ccctttaaca tcactcaccg cttcacgcac 1801 ctcttctggt ttggggatct taactaccgt gtggatctgc ctacctggga ggcagaaacc 1861 atcatccaga aaatcaagca gcagcagtac gcagacctcc tgtcccacga ccagctgctc 1921 acagagagga gggagcagaa ggtcttccta cacttcgagg aggaagaaat cacgtttgcc 1981 ccaacctacc gttttgagag actgactcgg gacaaatacg cctacaccaa gcagaaagcg 2041 acagggatga agtacaactt gccttcctgg tgtgaccgag tcctctggaa gtcttatccc 2101 ctggtgcacg tggtgtgtca gtcttatggc agtaccagcg acatcatgac gagtgaccac 2161 agccctgtct ttgccacatt tgaggcagga gtcacttccc agtttgtctc caagaacggt

FIG 15C

2221 cccgggactg ttgacagcca aggacagatt gagtttctca ggtgctatgc cacattgaag 2281 accaagtccc agaccaaatt ctacctggag ttccactcga gctgcttgga gagttttgtc 2341 aagagtcagg aaggagaaaa tgaagaagga agtgaggggg agctggtggt gaagtttggt 2401 gagactcttc caaagctgaa gcccattatc tctgaccctg agtacctgct agaccagcac 2461 atcctcatca gcatcaagtc ctctgacagc gacgaatcct atggcgaggg ctgcattgcc 2521 cttcggttag aggccacaga aacgcagctg cccatctaca cgcctctcac ccaccatggg 2581 gagttgacag gccacttcca gggggagatc aagctgcaga cctctcaggg caagacgagg 2641 gagaagctct atgactttgt gaagacggag cgtgatgaat ccagtgggcc aaagaccctg 2701 aagagcctca ccagccacga cccatgaag cagtgggaag tcactagcag ggcccctccg 2761 tgcagtggct ccagcatcac tgaaatcatc aaccccaact acatgggagt ggggcccttt 2821 gggccaccaa tgcccctgca cgtgaagcag accttgtccc ctgaccagca gcccacagcc 2881 tggagctacg accagccgcc caaggactcc ccgctggggc cctgcagggg agaaagtcct 2941 ccgacacctc ccggccagcc gcccatatca cccaagaagt ttttaccctc aacagcaaac 3001 cggggtctcc ctcccaggac acaggagtca aggcccagtg acctggggaa gaacgcaggg 3061 gacacgctgc ctcaggagga cctgccgctg acgaagcccg agatgtttga gaaccccctg 3121 tatgggtccc tgagttcctt ccctaagcct gctcccagga aggaccagga atcccccaaa 3181 atgccgcgga aggaaccccc gcccctgcccg gaaccccggca tcttgtcgcc cagcatcgtg 3241 ctcaccaaag cccaggaggc tgatcgcggc gagggcccg gcaagcaggt gcccgcgccc 3301 cggctgcgct ccttcacgtg ctcatcctct gccgagggca gggcggccgg cggggacaag

FIG 15D

```
3361 agccaaggga agcccaagac cccggtcagc tcccaggccc cggtgccggc caagaggccc 3421 atcaagcctt ccagatcgga aatcaaccag cagacccgc ccaccccgac gccgcggccg 3481 ccgctgccag tcaagagccc ggcggtgctg cacctccagc actccaaggg ccgcgactac 3541 cgcgacaaca ccgagctccc gcatcacggc aagcaccggc cggaggaggg gccaccaggg 3601 cctctaggca ggactgccat gcagtgaagc cctcagtgag ctgccactga gtcgggagcc 3661 cagagga
```

FIG 15E

MTTPRNSVNGTFPAEPMKGPIAMQSGPKPLFRRMSSLVGPTQSF
FMRESKTLGAVQIMNGLFHIALGGLLMIPAGIYAPICVTVWYPLWGGIMYIISGSLLA
ATEKNSRKCLVKGKMIMNSLSLFAAISGMILSIMDILNIKISHFLKMESLNFIRAHTP
YINIYNCEPANPSEKNSPSTQYCYSIQSLFLGILSVMLIFAFFQELVIAGIVENEWKR
TCSRPKSNIVLLSAEEKKEQTIEIKEEVVGLTETSSQPKNEEDIEIIPIQEEEEEETE
TNFPEPPQDQESSPIENDSSP

```
  1 gtacaaaaaa gcaggctcca ccatgacaac acccagaaat tcagtaaatg ggactttccc
 61 ggcagagcca atgaaaggcc ctattgctat gcaatctggt ccaaaaccac tcttcaggag
121 gatgtcttca ctggtgggcc ccacgcaaag cttcttcatg agggaatcta agactttggg
181 ggctgtccag attatgaatg ggctcttcca cattgccctg gggggtcttc tgatgatccc
241 agcagggatc tatgcaccca tctgtgtgac tgtgtggtac cctctctggg gaggcattat
301 gtatattatt tccggatcac tcctggcagc aacggagaaa aactccagga gtgtttggt
361 caaaggaaaa atgataatga attcattgag cctctttgct gccatttctg gaatgattct
421 ttcaatcatg gacatactta atattaaaat ttcccatttt ttaaaaatgg agagtctgaa
481 ttttattaga gctcacacac catatattaa catatacaac tgtgaaccag ctaatccctc
541 tgagaaaaac tccccatcta cccaatactg ttacagcata caatctctgt tcttgggcat
601 tttgtcagtg atgctgatct ttgccttctt ccaggaactt gtaatagctg gcatcgttga
661 gaatgaatgg aaaagaacgt gctccagacc caaatctaac atagttctcc tgtcagcaga
721 agaaaaaaaa gaacagacta ttgaaataaa agaagaagtg gttgggctaa ctgaaacatc
781 ttcccaacca aagaatgaag aagacattga aattattcca atccaagaag aggaagaaga
841 agaaacagag acgaactttc cagaacctcc ccaagatcag gaatcctcac caatagaaaa
901 tgacagctct cctttggacc cagctttctt gtac
```

FIG 16

METHODS FOR TREATING HEMATOPOIETIC MALIGNANCIES

This application claims priority to co-pending U.S. provisional Application Ser. No. 61/062,725, filed Jan. 28, 2008, which is herein incorporated by reference in its entirety for all purposes.

A Sequence Listing has been submitted in ASCII text file named 16915_ST25.txt, created on Feb. 25, 2013, consisting of 34.3 KB, the entire content of which is herein incorporated by reference.

This invention was made with government support under contract numbers T32 CA09523, K01 CA122192, R01 HL088686, and R01CA135531 awarded by the National Institutes of Health. The government has certain rights in the invention.

FIELD OF THE INVENTION

The present invention relates to methods for treating neoplasias in a mammalian subject. In particular, the present invention provides methods for treating lymphomas, including forms of non-Hodgkin lymphoma. In one embodiment, these methods involve reducing tumor necrosis factor-alpha signaling.

BACKGROUND OF THE INVENTION

Despite years of research into the development of new methods of treatment, cancers of the lymphatic system, or lymphomas, remain quite common. For example, more than 60,000 people in the United States are diagnosed with lymphoma each year, including more than 55,000 cases of non-Hodgkin lymphoma (NHL), and these numbers are constantly increasing. In addition, the prognosis for those affected by these diseases is often poor, as the survival rates for lymphoma patients remain low.

While traditional treatments for lymphoma typically depend on the type of lymphoma as well as the medical history of the patient, first-line treatments typically include chemotherapy. Such chemotherapy generally entails the administration of a mixture of compounds (e.g., the formulation referred to as CHOP that includes cyclophosphamide, doxorubicin, vincristine and prednisone. Cancer treatments also frequently include other forms of therapy (e.g., radiation). In many cases, patients respond initially to such first-line treatments, but subsequently suffer a relapse (e.g., tumor reappears or resumes growing). Following one such relapse, patients are often treated with further chemotherapy, or with other procedures such as bone marrow transplantation. Again, in many cases, patients initially respond to such additional treatments, but subsequently suffer another relapse. In other cases, a patient fails to respond at all to a treatment, even initially, and is thus said to have a refractory cancer. In such cases little agreement exists in the art regarding optimal subsequent treatment.

Thus there remains a need in the art for methods suitable for treating relapsing and/or refractory lymphomas, as well as for treating other poor-prognosis hematopoietic malignancies.

SUMMARY OF THE INVENTION

The present invention relates to methods for treating neoplasias in a mammalian subject. In particular, the invention provides methods for treating lymphomas, including forms of non-Hodgkin lymphoma. These methods involve reducing tumor necrosis factor-alpha signaling. Specifically, the present invention provides methods of treating a hematopoietic neoplasm in a human subject, comprising administering to the human subject an effective amount of a tumor necrosis factor-alpha (TNF-alpha) inhibitor. In some embodiments the TNF-alpha inhibitor is selected from the group consisting of an anti-TNF-alpha antibody and a soluble TNF-alpha receptor. In one embodiment, the TNF-alpha inhibitor comprises Pentoxifylline (Trental®).

In some embodiments, the anti-TNF-alpha antibody is a chimeric monoclonal antibody comprising a murine variable region or a TNF-binding portion thereof, and a human constant region. Anti TNF-alpha antibodies are exemplified by those described in U.S. Pat. Nos. 5,795,967, 5,223,395, 5,672,347, 6,537,549, 5,654,407, 6,649,589, 6,982,089, 6,419,944, and 6,379,666, including adalimumab (Humira®), and infliximab (Remicade®). In some preferred embodiments, the chimeric monoclonal antibody comprises infliximab (Remicade®). In some embodiments, the anti-TNF-alpha antibody is a humanized monoclonal antibody. In some embodiments, the anti-TNF-alpha antibody is a fully human monoclonal antibody. In some preferred embodiments, the human monoclonal antibody is adalimumab. In some embodiments, the soluble TNF-alpha receptor is a chimeric protein comprising human immunoglobulin G (IgG). In particular embodiments, the TNF-alpha receptor comprises eternacept (Enbrel®), an antagonistic soluble TNF-alpha receptor. In some preferred embodiments, the IgG fusion protein is etanercept. In additional preferred embodiments, the methods further comprise administering to the human subject a pharmaceutical composition comprising cyclophosphamide, doxorubicin, vincristine and prednisone (CHOP). In some embodiments, the methods further comprise administering to the human subject an anti-CD20 monoclonal antibody. In some preferred embodiments, the anti-CD20 monoclonal antibody is rituximab. In some embodiments, the hematopoietic neoplasm is a leukemia or a lymphoma. In some preferred embodiments, the lymphoma is a non-Hodgkin lymphoma. In some particularly preferred embodiments, the non-Hodgkin lymphoma is a diffuse large B-cell lymphoma (DLBCL) of an activated B-cell (ABC) subtype. In some embodiments, cells of the non-Hodgkin lymphoma express elevated levels of one or both of miR-21 and miR-155 in relation to germinal center B-cell (GCB) subtype lymphoma cells. In some embodiments, cells of the non-Hodgkin lymphoma express reduced levels of one or both of PTEN and SHIP-1 in relation to germinal center B-cell (GCB) subtype lymphoma cells.

The present invention also provides methods of treating a hematopoietic neoplasm in a human subject, comprising: a) detecting altered expression of one or more of miR-21, miR-155, PTEN, and SHIP-1 in cells of the hematopoietic neoplasm in relation to their expression in germinal center B-cell (GCB) subtype lymphoma cells; and b) administering to the human subject an effective amount of a tumor necrosis factor-alpha (TNF-alpha) inhibitor. In some embodiments, the hematopoietic neoplasm is a leukemia or a lymphoma. In some preferred embodiments, the lymphoma is a non-Hodgkin lymphoma. In some embodiments, the non-Hodgkin lymphoma is a diffuse large B-cell lymphoma (DLBCL). In some particularly preferred embodiments, the DLBCL is an activated B-cell (ABC) subtype DLBCL. Moreover, the present invention provides methods further comprising one or more of detecting increased expression of the miR-21, detecting increased expression of the miR-155, detecting reduced expression of the PTEN, and detecting reduced expression of the SHIP-1. In some embodiments the TNF-alpha inhibitor is selected from the group consisting of an anti-TNF-alpha antibody and a soluble TNF-alpha receptor. In some embodiments, the anti-TNF-alpha antibody is a chimeric monoclonal antibody comprising a murine variable region or a TNF-binding portion thereof, and a human constant region. In some preferred embodiments, the chimeric monoclonal antibody is infliximab. In some embodiments, the anti-TNF-alpha antibody is a humanized monoclonal antibody. In some embodiments, the anti-TNF-alpha antibody is a fully human monoclonal antibody. In some preferred embodiments, the human monoclonal antibody is adalimumab. In some embodiments, the soluble TNF-alpha receptor is a human immunoglobulin G (IgG) fusion protein. In some preferred embodiments, the IgG fusion protein is etanercept. In additional preferred embodiments, the methods further comprise administering to the human subject a pharmaceutical composition comprising CHOP. In some embodiments, the methods further comprise administering to the human subject an anti-CD20 monoclonal antibody. In some preferred embodiments, the anti-CD20 monoclonal antibody is rituximab.

BRIEF DESCRIPTION OF THE DRAWINGS

FIG. 3 provides a sequence alignment of the SHIP 3' UTR (SEQ ID NO:1) and miR-155 (SEQ ID NO:2). The sequence match in the crucial seed sequence is highlighted.

FIGS. 7A, 7B and 7C show that miR-21 and miR-155 expression levels are elevated, and that SHIP expression is reduced in specimens from patients with poor prognosis (ABC sub-type) diffuse large B cell lymphoma (DLBCL) as compared to the levels of specimens from patients with good prognosis (GC sub-type) DLBCL, respectively. Laser-capture-micro-dissection was performed on frozen lymph node sections from patients diagnosed with ABC DLBCL (n=6) or diagnosed with GC DLBCL (n=6). Quantitative-PCR (Q-PCR) analysis was done on 1000 cells/section using specific primers for miRs and SHIP. Q-PCR was normalized to U6B and GAPDH expression levels.

FIG. 9 shows that differential SHIP expression correlates with prognosis of DLBCL. (A) Two independent cDNA arrays (Alizadeh et al. (2000) Nature 403:503-511, Rosenwald et al. (2002) N Engl J Med 346:1937-1947), were analyzed in Oncomine on the world wide web oncomine.org for expression of SHIP in DLBCL, Chronic Lymphocytic Leukemia (CLL) and Follicular Lymphoma (FL). Y-axis represents normalized expression values (mean+/−standard deviation; p-values are derived from Student's t-test). (B) Kaplan-Meier plots (Oncomine; (7)) showing overall survival of 72 non-GC-DLBCL patients using defined cut-off values for SHIP expression (patient sub-groups defined as having the lowest 50% (50% low: 34 patients), lowest 25% (25% low: 18 patients) or lowest 10% (10% low: 7 patients) relative SHIP expression). (C) Sequence alignment of the SHIP 3' UTR and miR-155 (TargetScan; seed sequence is highlighted in gray). (D) Frozen lymph node sections of ABC (non-GC) and GC-DLBCL patients were stained with H&E, and tumor cells (>1000 cells/specimen) were isolated by Laser-Capture Microdissection. RNA was analyzed for miR-155, SHIP, U6 and GAPDH expression. Data represent 5 (GC) and 6 (non-GC) specimens, respectively (Wilcoxon rank sum test; p-value miR-155:0.08225; p-value SHIP:0.08125).

FIGS. 13A-B shows the coding and protein sequences of exemplary human TNF-alpha (GENBANK Accession No. NM_000594) (SEQ ID NOS: 4, 5).

FIGS. 14A-F shows the coding and protein sequences of exemplary human PTEN (GENBANK Accession No. NM_000314) (SEQ ID NOS: 6, 7).

FIGS. 15A-E shows the coding and protein sequences of exemplary human SHIP-1 (GENBANK Accession No. BC113582) (SEQ ID NOS: 8, 9).

FIG. 16 shows the coding and protein sequences of exemplary human CD20 (GENBANK Accession No. DQ896499) (SEQ ID NOS: 10, 11).

DEFINITIONS

Figure 1A:
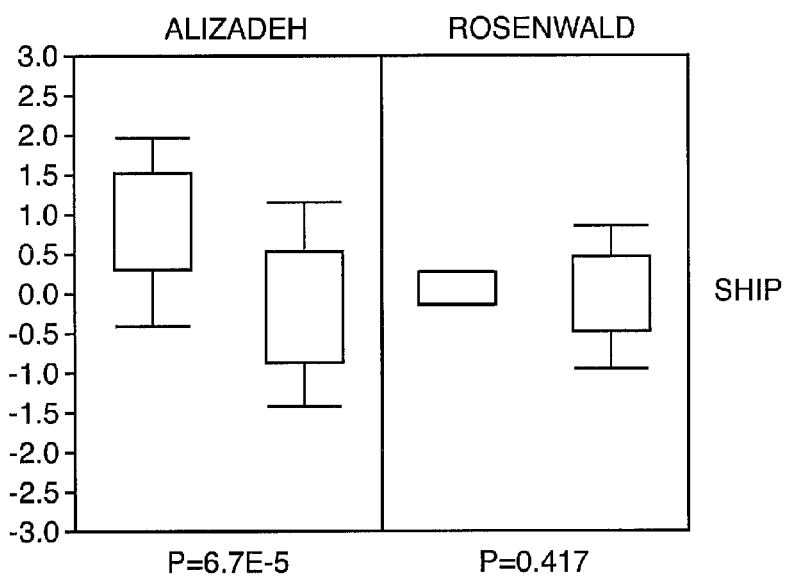
FIGS. 1A and 1B show that PTEN and SHIP expression are significantly down-regulated in diffuse large B cell lymphoma (DLBCL) as compared to chronic lymphocytic leukemia (CLL) and follicular lymphoma (FL) or CLL alone. The ONCOMINE program was used to query published cDNA array data. The results of two independent expression studies are shown (Alizadeh et al., Nature, 403:503-511, 2000; Lawrie et al., Int J Cancer, 121:1156-1161, 2007; Rosenwald et al., J Exp Med, 198:851-862, 2000; and Shipp et al., Nat Med, 8:68-74, 2002, all herein incorporated by reference). The Y-axis units are normalized expression values (standard deviations above and below the median per array, with P values indicated).

The terms "neoplasm" and "tumor" refer to a tissue growth that is characterized, in part, by increased angiogenesis and/or increased cell proliferation. This includes tissue that has aberrant growth of cells, tumors, malignant effusions, warts, polyps, nonsolid tumors, cysts and other growths. A site of neoplasia can contain a variety of cell types, including but not limited, to neoplastic cells, vascular endothelia, or immune system cells, such as macrophages and leukocytes, etc. Neoplasms may be benign or malignant. The terms "malignant neoplasm" and "malignant tumor" refer to a neoplasm that contains at least one cancer cell. A "cancer cell" refers to a cell undergoing early, intermediate or advanced stages of multi-step neoplastic progression as previously described (H. C. Pitot (1978) in "Fundamentals of Oncology," Marcel Dekker (Ed.), New York pp 15-28).

The term "cancer" in a mammal refers to any of a number of conditions caused by the abnormal, uncontrolled growth of cells. Cells capable of causing cancer, called "cancer cells", possess a number of characteristic properties such as uncontrolled proliferation, immortality, metastatic potential, rapid growth and proliferation rate, and certain typical morphological features. Often, cancer cells will be in the form of a tumor, but such cells may also exist alone within a mammal, or may be a non-tumorigenic cancer cell, such as a leukemia cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, AFP, HCG, CA 19-9, CA 15-3, CA 27-29, LDH, NSE, and others), and detecting a genotype indicative of a cancer (e.g., TP53, ATM, etc.). However, a negative result in one or more of the above detection methods does not necessarily indicate the absence of cancer, e.g., a patient who has exhibited a complete response to a cancer treatment may still have a cancer, as evidenced by a subsequent relapse.

The term "systemic delivery" as used herein, refers to delivery that leads to a broad bio-distribution of a compound within an organism. The term "systemic delivery," means that a useful, preferably therapeutic, amount of a compound is exposed to most parts of the body. To obtain broad bio-distribution generally requires a route of introduction such that the compound is not rapidly degraded or cleared (such as by first pass organs (liver, lung, etc.) or by rapid, nonspecific cell binding) before reaching a disease site.

"Hematopoietic neoplasm" refers to a neoplasm that is located in the blood and/or blood-forming tissue (such as the bone marrow, lymphatic tissue, etc.). The commonest forms are the various types of leukemia, of lymphoma, and of the progressive, life-threatening forms of the myelodysplastic syndromes. Hematopoietic neoplasms may originate from a hematopoietic cell of any lineage, including the lymphoid, myeloid and erythroid lineages. Hematopoietic neoplasms are exemplified by leukemia, lymphoma, multiple myeloma, myelodysplastic syndrome (MDS), myeloproliferative disease, and amyloid disease.

The term "leukemia" refers to a progressive, malignant disease of the blood or bone marrow, characterized by abnormal proliferation and development of blood cells, usually white blood cells (leukocytes). Leukemias are classified according to the degree of cell differentiation as acute or chronic, and according to predominant type of cell involved as myelogenous or lymphatic. Leukemias are exemplified by acute lymphocytic leukemia (ALL), chronic myelogenous leukemia (CML), acute myeloid leukemia (AML), chronic lymphocytic leukemia (CLL), hairy cell leukemia, etc.

The term "lymphoma" refers to a malignant growth of B or T cells in the lymphatic system, presenting as an enlargement of the node (a tumor). The term "lymphoma" includes numerous types of malignant growths, including Hodgkin's lymphoma and non-Hodgkin lymphoma (NHL).

"Hodgkin lymphomas" are exemplified by classical Hodgkin lymphomas and nodular lymphocyte-predominant Hodgkin lymphoma.

The term "non-Hodgkin lymphoma" refers to a malignant growth of B or T cells in the lymphatic system that is not otherwise classified as a Hodgkin's lymphoma (e.g., having Reed-Sternberg cells in the cancerous area). Non-Hodgkin lymphomas encompass over 29 types of lymphoma, the distinctions between which are based on the type of cancer cells. The particular classification depends on the particular system of classification used, such as the Working formulation, the Rappaport classification, and the REAL classification. In preferred embodiments, the REAL classification is used. For example, Non-Hodgkin lymphomas include mature B cell neoplasms and T cell and natural killer cell neoplasms. Mature B cell neoplasms are exemplified by diffuse large B-cell lymphoma (DLBCL), B-cell prolymphocytic leukemia, lymphoplasmacytic lymphoma (such as Waldenström macroglobulinemia), splenic marginal zone lymphoma, plasma cell neoplasms, extranodal marginal zone B cell lymphoma (also called MALT lymphoma), nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, and Burkitt lymphoma/leukemia. Mature T cell and natural killer (NK) cell neoplasms are exemplified by T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/Sezary syndrome, primary cutaneous CD30-positive T cell lymphoproliferative disorders, angioimmunoblastic T cell lymphoma, peripheral T cell lymphoma, unspecified, and anaplastic large cell lymphoma.

The term "relapsed cancer" or "relapsed lymphoma" refers to a cancer or lymphoma that has recurred following prior complete or partial remission in response to a prior treatment. Recurrence can be defined in any way, including a reappearance or re-growth of a tumor as detected by clinical, radiological, or biochemical assays, or by an increased level of a cancer marker. Prior treatments can include, but are not limited to, chemotherapy, radiation therapy, and bone marrow transplantation.

The term "indolent" non-Hodgkin lymphoma is a classification that includes slow growing forms of lymphoma. They encompass what are called low grade and some categories of intermediate grade NHL. Indolent NHLs are sometimes not responsive to conventional cancer therapies such as chemotherapy and radiation therapy.

Patients with "refractory cancer" or "refractory lymphoma" are those who have failed to achieve complete remission on their first course of combination chemotherapy, or to patients who have failed to achieve complete or partial remission on subsequent chemotherapy. "Primary refractory" patients are those who have never achieved complete remission even at first treatment.

A "stable disease" is a state wherein a therapy causes cessation of growth or prevalence of a tumor or tumors as measured by the usual clinical, radiological and biochemical means, although there is no regression or decrease in the size or prevalence of the tumor or tumors, i.e., cancer that is not decreasing or increasing in extent or severity.

"Partial response" or "partial remission" refers to the amelioration of a cancerous state, as measured by tumor size and/or cancer marker levels, in response to a treatment. Typically, a "partial response" means that a tumor or tumor-indicating blood marker has decreased in size or level by about 50% in response to a treatment. The treatment can be any treatment directed against cancer, but typically includes chemotherapy, radiation therapy, hormone therapy, surgery, cell or bone marrow transplantation, immunotherapy, and others. The size of a tumor can be detected by clinical or by radiological means. Tumor-indicating markers can be detected by means well known to those of skill (e.g., ELISA or other antibody-based tests).

A "complete response" or "complete remission" means that a cancerous state, as measured by, for example, tumor size and/or cancer marker levels, has disappeared following a treatment such as chemotherapy, radiation therapy, hormone therapy, surgery, cell or bone marrow transplantation, or immunotherapy. The presence of a tumor can be detected by clinical or by radiological means. Tumor-indicating markers can be detected by means well known to those of skill (e.g., ELISA or other antibody-based tests). A "complete response" does not necessarily indicate that the cancer has been cured, however, as a complete response can be followed by a relapse.

The term "chemotherapy" refers to the administration of chemical agents that inhibit the growth, proliferation and/or survival of cancer cells. Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapy can include any chemical agent that inhibits, or is designed to inhibit, a cancerous cell or a cell likely to become cancerous. Such agents are often administered, and are often most effective, in combination (e.g., CHOP formulation).

The term "radiation therapy" refers to the administration of radioactivity to an animal with cancer. Radiation kills or inhibits the growth of dividing cells, such as cancer cells.

The term "immunotherapy" refers to methods of enhancing the ability of an animal's immune system to destroy cancer cells within the animal.

As used herein the terms "tumor necrosis factor-alpha," "TNF-alpha" and "cachectin" refer to a multifunctional proinflammatory cytokine secreted predominantly by monocytes/macrophages that has effects on lipid metabolism, coagulation, insulin resistance, and endothelial function. The coding and protein sequences of exemplary human TNF-alpha are described in GENBANK Accession No. NM_000594 (SEQ ID NOS: 4, 5).

As used herein the terms "microRNAs" and "miRNAs" refer to endogenous noncoding RNAs of about 22 nucleotides that regulate mRNAs by targeting them for cleavage or translational repression. The sequence of "miR-155" is 3' GGG-GAUAGUGCUAAUCGUAAUU-5' (SEQ ID NO:2). The sequence of "miR-21" is 5'- AGUUGUAGUC AGACUA-UUCG AU -3' (SEQ ID NO:3).

The terms "phosphatase and tensin homolog" deleted on chromosome ten, "PTEN," "mutated in multiple advanced cancers 1" and "MMACI" refer to a tumor suppressor protein having a tyrosine phosphatase domain and a region of homology to tensin. The coding and protein sequences of exemplary human PTEN are described in GENBANK Accession No. NM_000314 (SEQ ID NOS: 6, 7).

The terms "SH2-containing inositol phosphatase," "SHIP-1" "inositol polyphosphate-5-phosphatase" and "1NPP5D" refer to an enzymes that hydrolyzes inositol 1,4,5-triphosphate in a signal-terminating reaction. The coding and protein sequences of exemplary human SHIP-1 are described in GENBANK Accession No. BC113582 (SEQ ID NOS: 8, 9).

The terms "B-lymphocyte surface antigen B 1," "B 1" and "CD20" refer to an antigen having four highly conserved transmembrane domains, flanked by N- and C-terminal cytoplasmic regions, which is widely expressed during B-cell development from early pre-B cell stages until differentiation into plasma cells. The coding and protein sequences of exemplary human CD20 are described in GENBANK Accession No. DQ896499 (SEQ ID NOS: 10, 11).

Polyclonal antibodies are heterogeneous populations of antibody molecules derived from the sera of animals immunized with an antigen. A monoclonal antibody (mAb) contains a substantially homogeneous population of antibodies specific to antigens, which population contains substantially similar epitope binding sites. MAbs may be obtained by methods known to those skilled in the art (e.g., Kohler and Milstein, Nature 256:495-497, 1975; Ausubel et al., eds., Current Protocols in Molecular Biology, Greene Publishing Assoc. and Wiley Interscience, NY, 1992; and Harlow and Lane, Antibodies: A Laboratory Manual Cold Spring Harbor Laboratory, 1988; Colligan et al., eds., Current Protocols in Immunology, Greene Publishing Assoc. and Wiley Interscience, NY, 1993; the contents of which are incorporated herein in their entirety). Such antibodies may be of any immunoglobulin class including IgG, IgM, IgE, IgA, and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., Proc Natl Acad Sci USA, 81:3273-3277, 1984; Morrison et al., Proc Natl Acad Sci USA, 81:6851-6855, 1984; Boulianne et al., Nature, 312: 643-646, 1984; Neuberger et al., Nature, 314:268-270, 1985;

Sahagan et al., J Immunol, 137:1066-1074, 1986; Liu et al., Proc Natl Acad Sci USA, 84:3439-3443, 1987; Sun et al., Proc Natl Acad Sci USA, 84:214-218, 1987; Better et al., Science, 240:1041-1043, 1988; and Harlow and Lane, Antibodies: A Laboratory Manual, Cold Spring Harbor Laboratory, 1988).

Anti-TNF antibodies of the present invention can include at least one of a heavy chain constant region (Hc), a heavy chain variable region (Hv), a light chain variable region (Lv) and a light chain constant region (Lc), wherein a polyclonal Ab, monoclonal Ab, fragment and/or regions thereof include at least one heavy chain variable region (Hv) or light chain variable region (Lv) which binds a portion of a TNF and inhibits and/or neutralizes at least one TNF biological activity.

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a Hc region that aggregates (e.g., IgM H chain).

Murine and chimeric antibodies, fragments and regions of the present invention comprise individual heavy (H) and/or light (L) immunoglobulin chains. A chimeric H chain comprises an antigen-binding region derived from the H chain of a non-human antibody specific for TNF, which is linked to at least a portion of a human Hc region, such as $CH_1$ or $CH_2$. A chimeric L chain according to the present invention comprises an antigen-binding region derived from the L chain of a non-human antibody specific for TNF, linked to at least a portion of a human Lc region.

The terms "treating," "treatment" and grammatical equivalents when in reference to a disease (e.g., cancer) encompasses delaying and/or reducing one or more objective symptoms (such as tumor size, blood or urine levels of metabolic compounds such as glucose, body weight, etc.) and/or subjective symptoms (e.g., pain, fatigue, difficulty in breathing, clarity of vision, nausea, etc.) of the disease.

When in reference to the level of molecules and/or phenomena, the terms "reduce," "inhibit," "diminish," "suppress," "decrease," and grammatical equivalents (including "lower," "smaller," etc.) when in reference to the level of any molecule (such as SHIP, miR-21, miR155, TNF-alpha, anti-TNF-alpha antibody, TNF-alpha receptor, etc., and nucleic acid sequences encoding any of the polypeptides described herein), and/or phenomenon (e.g., cell number, cell death, cell apoptosis, cell viability, cell survival, binding to a molecule, affinity of binding, expression of a nucleic acid sequence, transcription of a nucleic acid sequence, enzyme activity, etc.) in a first sample relative to a second sample, mean that the quantity of molecule and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, fatigue, difficulty in breathing, clarity of vision, nausea, etc. In another embodiment, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample.

When in reference to the level of molecules and/or phenomena, the terms "increase," "elevate," "raise," and grammatical equivalents (including "higher," "greater," etc.) when in reference to the level of any molecule (such as SHIP, miR-21, miR155, TNF-alpha, anti-TNF-alpha antibody, TNF-alpha receptor, etc., and nucleic acid sequences encoding any of the polypeptides described herein), and/or phenomenon (e.g., cell number, cell death, cell apoptosis, cell viability, cell survival, binding to a molecule, affinity of binding, expression of a nucleic acid sequence, transcription of a nucleic acid sequence, enzyme activity, etc.) in a first sample relative to a second sample, mean that the quantity of the molecule and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, fatigue, difficulty in breathing, clarity of vision, nausea, etc. In another embodiment, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

"Subject" and "animal" include mammals, such as humans and non-human mammals that include primates, murines, ovines, bovines, ruminants, lagomorphs, porcines, caprines, equines, canines, felines, guinea pig, hamster, ferret, chinchilla, mouse and cotton rat.

"Tumor necrosis factor-alpha (TNF-alpha) inhibitor" refers to a molecule that reduces the level of binding of TNF-alpha to its receptor by any statistically significant amount, including a reduction in binding to a quantity that is at least 10% lower than, at least 25% lower than, at least 50% lower than, at least 75% lower than, and/or at least 90% lower than the quantity of binding when compared to the quantity of binding in the absence of the TNF-alpha inhibitor. TNF-alpha inhibitors are exemplified by anti-TNF-alpha antibody, TNF-alpha receptor, and other compounds, such as Pentoxifylline, which is the International Nonproprietary Name (INN) of a is a xanthine derivative drug sold by Aventis under the name Trental®. Its chemical name is 1-(5-oxohexyl)-3,7-dimethylxanthine.

The terms "chimeric" and "fusion" when in reference to a protein refer to a protein that contains at least two amino acid sequences that are operably linked together. The amino acid sequences may be derived from different sources (e.g., different organisms, different tissues, different cells, etc.) or may be different sequences from the same source. In one embodiment, the chimeric protein is a recombinant protein that is produced by expressing operably linked nucleotide sequences that encode the amino acid sequences. The term "operably linked" when in reference to the relationship between nucleic acid sequences and/or amino acid sequences refers to linking the sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. The term also refers to the linkage of amino acid sequences in such a manner so that a functional protein is produced.

"Pentoxifylline" is the generic name of the brand name drug "Trental®." It is a tri-substituted xanthine derivative designated chemically as 1-(5-oxohexyl)-3,7-dimethylxanthine (CAS Registry Number 6493-05-6).

"Adalimumab" and "Humira®" refer to a recombinant human IgG1 monoclonal antibody specific for human tumor necrosis factor (TNF). Humira® was created using phage display technology resulting in an antibody with human derived heavy and light chain variable regions and human IgG1:K constant regions. Adalimumab is produced by recombinant DNA technology in a mammalian cell expression system and is purified by a process that includes specific viral inactivation and removal steps. It consists of 1330 amino acids and has a molecular weight of approximately 148 kilodaltons.

"Infliximab" and "Remicade®" refer to a chimeric IgG1κ monoclonal antibody with an approximate molecular weight of 149,100 daltons. It is composed of human constant and murine variable regions. Infliximab binds specifically to human tumor necrosis factor alpha (TNFα) with an association constant of 1010 M−1. Infliximab is produced by a recombinant cell line cultured by continuous perfusion and is purified by a series of steps that includes measures to inactivate and remove viruses.

"Etanercept," "eternacept" and "Enbrel®" interchangeably refer to a dimeric fusion protein consisting of the extracellular ligand-binding portion of the human 75 kd (p75) tumor necrosis factor receptor (TNFR) linked to the Fc portion of human IgG1. The Fc component of etanercept contains the $C_H2$ domain, the $C_H3$ domain and hinge region, but not the $C_H1$ domain of IgG1. Etanercept is produced by recombinant DNA technology in a Chinese hamster ovary (CHO) mammalian cell expression system. It consists of 934 amino acids and has an apparent molecular weight of approximately 150 KD.

DETAILED DESCRIPTION OF THE INVENTION

Data herein (Examples 1-6) identifies the inositol phosphatase SHIP, a previously unidentified tumour suppressor, as a bona-fide target of the oncogenic miR-155, an onco-miR whose expression in B cells alone is sufficient to trigger malignant transformation. In particular, data herein demonstrate that in diffuse large B cell lymphoma (DLBCL), elevated levels of miR-155, and consequent diminished SHIP expression are the result of autocrine stimulation by the pro-inflammatory cytokine TNF-alpha. Anti-TNF-alpha regimen such as eternacept or infliximab were sufficient to reduce miR-155 levels and restored SHIP expression in DLBCL cells with an accompanying reduction in cell proliferation. Furthermore, data herein demonstrate a substantial decrease in tumor burden in DLBCL xenografts in response to eternacept. This data strongly support the concept that cytokine-regulated inflammatory miRs can function as a link between inflammation and cancer, can contribute to the development and/or progression of cancer, and illustrate the feasibility of anti-TNF-alpha therapy as a novel and immediately accessible treatment for hematopoietic cancers, such as DLBCL, alone or in combination with other treatments for DLBCL.

While an understanding of the mechanism of action of the invention is not necessary, and without limiting the invention to any particular mechanism, it is the inventors' view that aberrant miR-155 expression in non-GC-DLBCL appears to be the result of an autocrine stimulation by TNF-alpha, as miR-155 and SHIP levels can be reduced or increased, respectively, through the administration of neutralizing anti-TNF-alpha antibodies or soluble TNF-alpha receptor.

B cell survival and fate determination are strongly dependent upon phosphatidylinositol 3-kinase (PI3K) signalling (Fruman et al. (2004) Curr Opin Immunol 16:314-320, Alizadeh et al. (2000) Nature 403:503-511). PI3K catalyzes the conversion of membrane phosphatidylinositol-(4,5)-bisphosphate to phosphatidylinositol-(3,4,5)-trisphosphate (PIP3), which acts as a second messenger to recruit pleckstrin-homology domain containing adapters and kinases such as PDK, AKT, PLCγ2, BTK, DOK, and others. Subsequent activation/inactivation of additional effectors including SGK, TOR, PP2A, FOXO, and Cyclin D/E mediates diverse biological responses such as survival, proliferation, migration, adhesion, and differentiation.

PI3K signals are antagonized by two lipid phosphatases: the 3'-inositol phosphatase PTEN and the 5'-inositol phosphatase SHIP. Mills et al. recently discovered that in contrast to T cells, B cells do not undergo malignant transformation upon PTEN deletion; similarly, deletion of SHIP in B cells is insufficient to generate B cell lymphoma. However, concomitant ablation of both SHIP and PTEN in murine B cells induces lethal lymphoma resembling DLBCL with 100% penetrance, revealing a novel role for SHIP as a tumor-suppressor (Mills et al., manuscript in preparation).

DLBCL is clinically, morphologically and genetically a heterogeneous group of malignant proliferation of large lymphoid B cells that accounts for approximately 40% (25,000 cases/yr) of adult non-Hodgkin lymphomas (3). Standard chemotherapy has been recently expanded from CHOP (Cyclophosphamide/Doxorubicin/Vincristine/Prednisolone) to R-CHOP with the inclusion of Rituximab, an anti-CD20 monoclonal antibody, which improved treatment success to an overall 3-year relapse free survival of DLBCL patients at 53-63.1% (Habermann et al. (2006) J Clin Oncol 24:3121-3127, Pfreundschuh et al. (2008) Lancet Oncol 9:435-4444). Two prognostically different subgroups of DLBCL have been identified with distinct gene expression profiles either characteristic of normal germinal center B cells or of activated memory B cells. The germinal center B-cell-like (GC) subgroup was correlated with a significantly better prognosis (5-year survival: 76%) in comparison to the activated B-cell-like (ABC or non-GC) subgroup (5-year survival: 16%) (Alizadeh et al. (2000) Nature 403:503-511, Shipp et al (2002) Nat Med 8:68-74).

Recently, SHIP-1 has been identified as a tumor suppressor. Now as described herein, poor-prognosis large B-cell lymphomas were found express lower levels of SHIP-1, which is a target for the micro-RNA miR-155. Ectopic overexpression of miR-155 has been shown to cause lymphomas in mice (Costinean et al., Proc Natl Acad Sci USA, 103:7024-7029, 2006), and miR-155 RNA has been shown to accumulate in various types of human B cell lymphoma (Eis et al., Proc Natl Acad Sci USA, 102:3627-3632, 2005). In addition, miR-155 expression has been shown to be can be induced by TNF-alpha (O'Connell et al., Proc Natl Acad Sci USA, 104: 1604-1609, 2007). Now as determined during development of the present invention, reducing TNF-alpha signaling in poor-prognosis large B-cell lymphoma cells leads to the down-regulation of miR-155 and consequent up-regulation of SHIP-1. Thus reducing TNF-alpha signaling provides a new and counter-intuitive therapy for poor-prognosis large B-cell lymphomas and other hematopoietic malignancies.

I. Lymphoma

Disease in B cell non-Hodgkin lymphoma (NHL) patients is graded according to the International Prognostic Index (IPI), which assigns low scores for the involvement of single lymph nodes, intermediate scores for multiple lymph node involvement, and high scores for systemic nodal and non-lymphoid metastases (See, e.g., Blood, 89:3909-3918, 1997). Diffuse large B-cell lymphoma (DLBCL) accounts for approximately 40% of adult non-Hodgkin lymphomas. DLBCL is clinically, morphologically and genetically a heterogeneous group of tumors composed of large B cells. Several microarray studies performed on untreated, de novo DLBCL, identified two main, prognostically different subgroups (Alizadeh et al., Nature, 403-503-511, 2000). Both were characterized by a distinct gene expression profile either characteristic of normal germinal center B-cells or of activated blood memory B-cells. The germinal center B-cell-like (GCB-like) subgroup was correlated with a significantly better prognosis in comparison to the activated B-cell-like (ABC-like) subgroup (Rosenwald et al., N Engl J Med, 346: 1937-1947, 2002; and Rosenwald et al., J Exp Med, 198:851-862, 2003). In particular the five-year overall survival rate for the GCB-like is 70%, while the rate for the ABC-like group is 12%.

Standard chemotherapy has been recently expanded from cyclophosphamide/doxorubicin/vincristine/prednisolone (CHOP) formulation to R-CHOP with the further inclusion of rituximab (See, e.g., U.S. Pat. No. 7,244,450 to Sarris et al., herein incorporated by reference). Rituximab is an anti-CD20 monoclonal antibody (See, e.g., U.S. Pat. No. 5,736,137 to Anderson et al., herein incorporated by reference). Rituximab, which is marketed as RITUXIN by Genentech, South San Francisco, Calif. and Biogen Idec, Cambridge, Mass., has improved treatment success of specific DLBCL subgroups. Although this B cell-depleting/inactivating monoclonal antibody has greatly advanced DLBCL therapy and significantly slowed disease progression in certain patient subgroups with low IPI scores, the lifespan of high-risk patients with disseminated lymphoma is not significantly extended by this treatment. Significant effort toward understanding disease progression in human patients has suggested that B cell NHL, in addition to multiple cancer-promoting genetic hits is fueled by non-specific stimuli, and B cell antigen receptor-mediated recognition of undefined self-antigens. In support of this latter idea, B-cell NHL tumors often display several hallmarks of antigen-mediated clonal selection. Additionally, B-cell NHL patients often have high serum autoantibody titers, suggesting autoantigen-mediated terminal differentiation.

II. microRNAs (miRNAs) and Cancer

Soon after the discovery of the first mammalian miRNA some 12 years ago, it became evident that this class of molecules plays a critical role in global gene regulation, and likely impacts cellular survival and death pathways. More recently high throughput analyses have demonstrated that miRNA expression is commonly dysregulated in a multitude of human cancers (Calin, Nature Rev, 6:957-866, 2996; Lu, Nature, 435:834-838, 2005; and Roldo, J Clin Invest, 24:4677-4684, 2006), and miRNA expression profiling has shown promise in defining malignant status in retrospective studies.

Interestingly, more than 50% of annotated human miR genes are located in fragile chromosomal regions that are susceptible to amplification, deletion, or translocation during the course of tumor development (Calin, Proc Natl Acad Sci USA, 101:2999-3004, 2004). Moreover, recent evidence indicates that some miRs functions either as oncogenes or tumor suppressors (Eswuela-Kerscher, Nature Rev Cancer, 6:259-269, 2006; He, Nature, 435:828-833, 2005; and Johnson, Cell, 120:635-647, 2005). The first study documenting abnormalities in miRNA expression in tumor samples focused on chronic lymphocytic leukemia (CLL). Deletion of chromosome 13q14 is the most frequent chromosomal abnormality in this disorder. Croce and co-workers demonstrated that tumor suppressor activity is likely provided by two miRNAs, miR-15a and miR-16-1 (Calin et al., Proc Natl Acad Sci USA, 99:15524-15529, 2002). In addition, a conserved site for miR-15a and miR-16-1 was identified in the 3' UTR of the bcl-2 mRNA, which encodes the anti-apoptotic protein Bcl-2. Loss of miR-15a and miR-16-1 are thought to contribute to elevated Bcl-2 expression and pathological cell survival in CLL (Cimmino et al., Proc Nat Acad Sci USA, 102:13944-13949, 2005). In contrast, the miR-17-92 polycistron is located in a region of DNA that is amplified in human B cell lymphomas (Ota et al., Cancer Res, 64:3087-3095, 2004), and enforced expression of the miR-17-92 cluster acts to accelerate tumor development in mouse B cell lymphoma (He et al., Nature, 435:828-833, 2005). Similarly, miR-17-5p and miR-20a have been demonstrated to control the balance of cell death and proliferation through c-myc (O'Donnell, Nature, 435:839-843, 2005) and the miR-34 family of microRNAs has been found to target the tumor suppressor gene p53 thereby encouraging inappropriate cell proliferation. In addition, miR-10b is highly expressed in breast cancer and has recently been found to inhibit the translation of the homeobox gene D10 resulting in increased expression of the pro-metastatic gene RHOC (Ma, Nature, 499:682-688, 2007).

Several studies have illustrated the importance of miRs in B cell lymphomas. For instance, miR-155 was found to be highly expressed in Hodgkin lymphoma and DLBCL (Lawrie et al., Expert Opin Biol Ther, 7:1363-1374, 2007; Lawrie et al., Br J Haematol, 137:503-512, 2007; and Eis et al., Proc Natl Acad Sci USA, 102:3627-3632, 2005). Using a prototypic cell line model of the GCB and ABC subtypes of DLBCL, microRNAs miR-221 and miR-21 as well as miR-155 were found to be over-expressed in ABC-type but not GCB-type lymphoma cells. In addition, these microRNAs were found to be over-expressed in clinical cases of DLBCL and FCL, and in DLBCL cases that had undergone high-grade transformation from previously diagnosed FCL. Consistent with the cell line model, these microRNAs were more highly expressed in de novo DLBCL cases that were immunophenotypically classified as ABC-type than those that were classified as GCB-type. While many of these studies are of a correlative nature, conclusive proof for the oncogenic potential of miRs has been demonstrated by transgenic expression of miR-155, resulting in a preleukemic pre-B cell proliferation evident in spleen and bone marrow, followed by frank B cell malignancy (Costinean et al., Proc Natl Acad Sci USA, 103:7024-7029, 2006). This direct evidence that overexpression of a miRNA can result in the development of a neoplastic disease, highlighting the potential role of miRNA in human malignancies.

III. Regulation of Lipid Phosphatases and Cancer

Figure 1B:
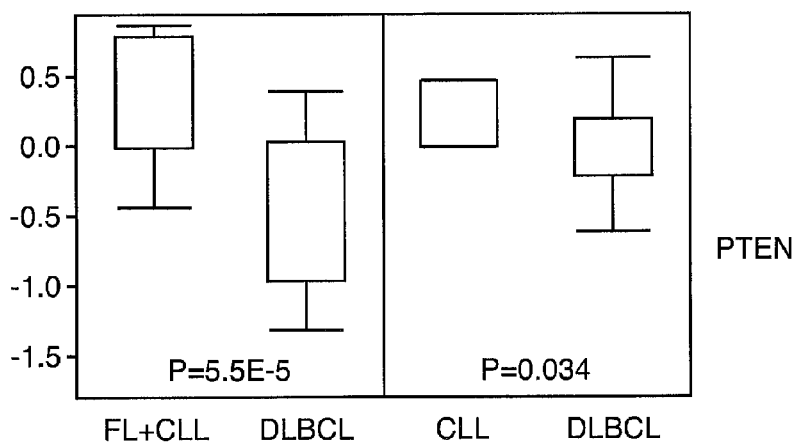
Figure 2:
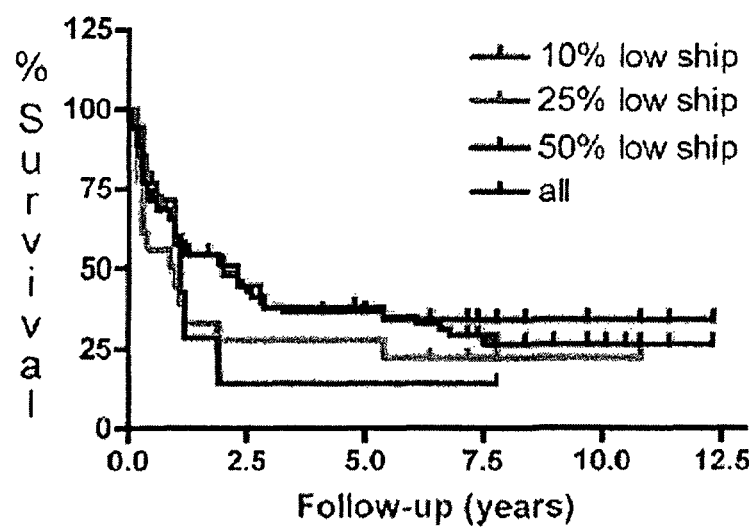
FIG. 2 illustrates that low SHIP expression levels correlate with poor survival of DLBCL patients as determined through analysis of the published cDNA array data using the ONCOMINE program. The graph shown is a Kaplan-Meier plot of overall survival of DLBCL patients using defined cut-off values for SHIP.
Figure 4A:
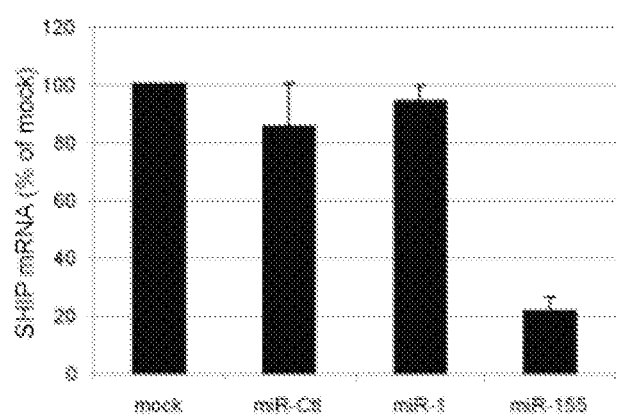
FIGS. 4A and 4B provide graphs showing that miR-155 regulates SHIP expression levels. CEM cells were transfected with 50 □M of a non-specific control miR, miR-1, miR-155, anti-control miR, or anti-miR155. SHIP mRNA levels were determined by QPCR after 12 hours.
Figure 4B:
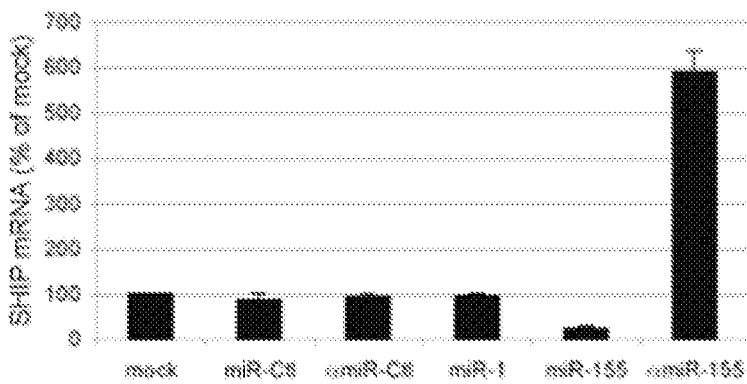

Survival of all cell types is mediated by phosphatidylinositol-3-kinase (PI3K) signaling, and is important in B cell fate determination. PI3K signals are antagonized by two lipid phosphatases PTEN and SHIP. To determine if attenuated SHIP expression occurs in human B cell malignancies, during development of the present invention, the ONCOMINE program was used to query published cDNA array data (Rhodes et al., Neoplasia, 6:1-6, 2004; Rhodes et al., Proc Natl Acad Sci USA, 101:9309-9314, 2004; Rhodes et al., Nat Genet, 37:579-583, 2005; and Rhodes et al., Neoplasia, 9:166-180, 2007). In particular the ONCOMINE program was utilized to look for a correlation between expression profiles of PTEN and/or SHIP, and prognosis of patients with B cell tumors. Through analysis of the data sets provided by two groups (Alizadeh Nature, 403:503-511, 2000; and Rosenwald et al., J Exp Med, 198:851-862, 2003) expression of both SHIP and PTEN was found to be significantly reduced in different human lymphoma patient specimens, such as Diffuse Large B-Cell Lymphoma (DLBCL) or Follicular Lymphoma (FL), as compared to normal tissue. In addition, the levels of both tumor suppressor genes were found to be reduced in a pattern that correlated with the aggressiveness of the hematological malignancy. Specifically as described herein, the more indolent diseases such as CLL (Chronic Lymphocytic Leukemia), and (FL) (Follicular Lymphoma) express significantly higher levels of PTEN and SHIP, as compared to the more aggressive B cell malignancy DLBCL (Diffuse Large B cell Lymphoma) (FIG. 1). Furthermore, the expression levels of PTEN or SHIP were found to be lowest in patients of the ABC subgroup of DLBCL patients, as compared to the GCB subgroup of patients. Further analysis of the published cDNA array data revealed that SHIP expression levels in DLBCL specimens correlate with overall patient survival (FIG. 2).

To explore whether the reduced SHIP expression in DLBCL, particularly of the ABC subtype were a consequence of misexpression of cellular microRNAs (miRNAs), algorithms provided by the miRBase were used to identify miRNAs likely to target SHIP. As shown in FIG. 3, the 3' UTR of the SHIP mRNA was found to contain a very promising target site for onco-miR 155. Indeed transfection of a synthetic mimic of miR-155, but not a non-specific control miRNA or an irrelevant miRNA (e.g., miR-1) was found to substantially attenuate SHIP expression. Conversely introduction of a neutralizing anti-miR against miR-155 caused a significant increase in SHIP mRNA levels.

miR-155 is one of only a few microRNAs whose expression had been shown to be regulated by extracellular ligands (O'Connell et al., Proc Nat Acad Sci USA, 104:1604-1609, 2007). In particular, miR-155 expression can be induced in macrophages by stimulation with lipopolysaccharide (LPS) or tumor necrosis factor-alpha (TNFα). Analysis of the activation pathway indicated that miR-155 is an NFκB-responsive transcript. Strikingly, the cDNA array studies that characterized DLBCL based on distinct gene expression profiles found that poor-prognosis ABC subtype cells displayed a gene expression profile consistent with elevated NFκB activation. Accordingly, the premise that TNFα induces miR-155 in B cells was tested during development of the present invention by exposing splenic B cell from wild type mice with TNFα in vitro. Indeed TNFα exposure induced expression of miR-155 in primary murine B cells.

Figure 5A:
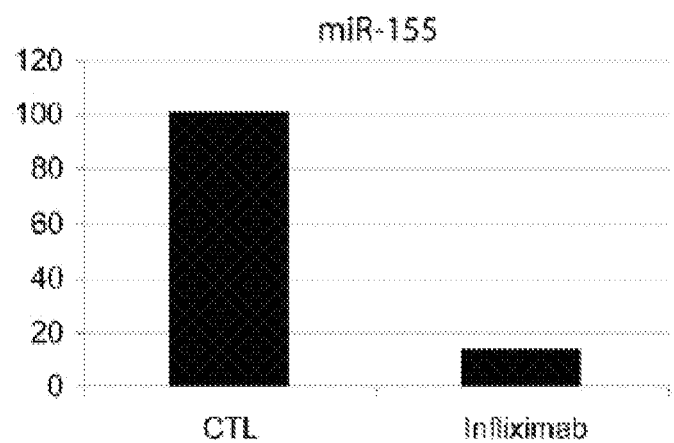
FIGS. 5A and 5B provide graphs showing a tumor necrosis factor-alpha (TNF-alpha)-mediated auto-stimulatory loop in ABC-like DLBCL cells. Toledo cells were cultured in the presence or absence of 5 ng/ml of an anti-TNF-alpha monoclonal antibody (infliximab) for 8 hours, before isolation of total RNA and determination of miR-155 and SHIP mRNA expression levels by QPCR.
Figure 5B:
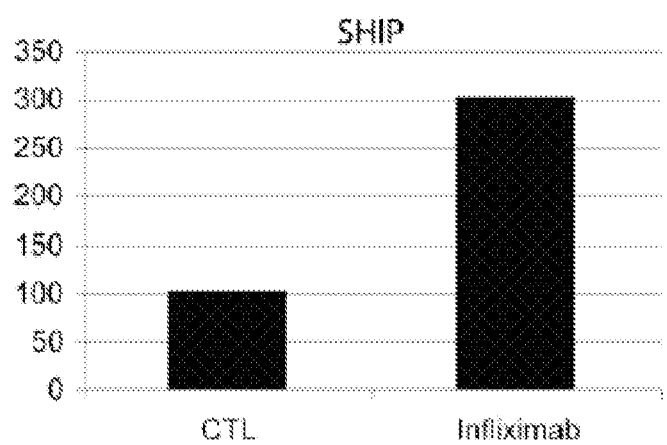
Figure 6:
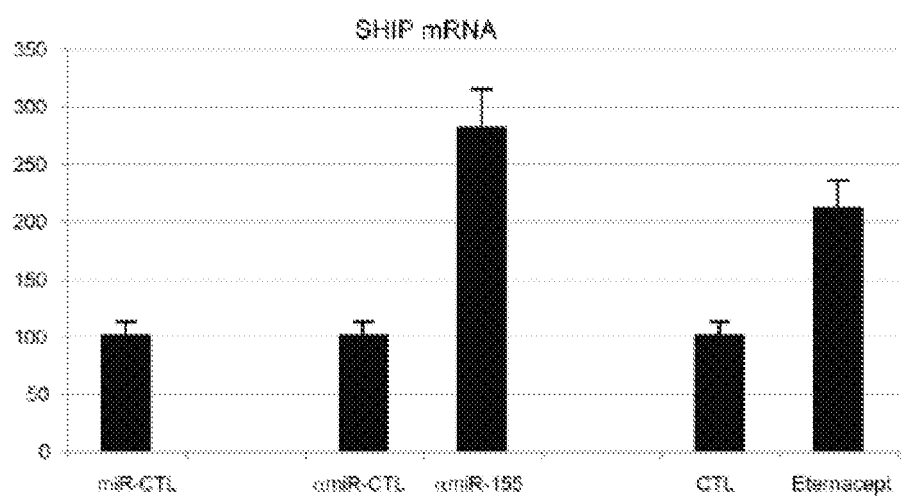
FIG. 6 provides a graph further illustrating a TNF-alpha-mediated auto-stimulatory loop in ABC-like DLBCL cells. Toledo cells were cultured in the presence or absence of 100 ng/ml of a soluble TNF-alpha receptor antagonist (eternacept) for 24 hours prior to analysis of SHIP mRNA expression levels. Transfection of cells with anti-miR-155 was included for comparison.
Figure 8:
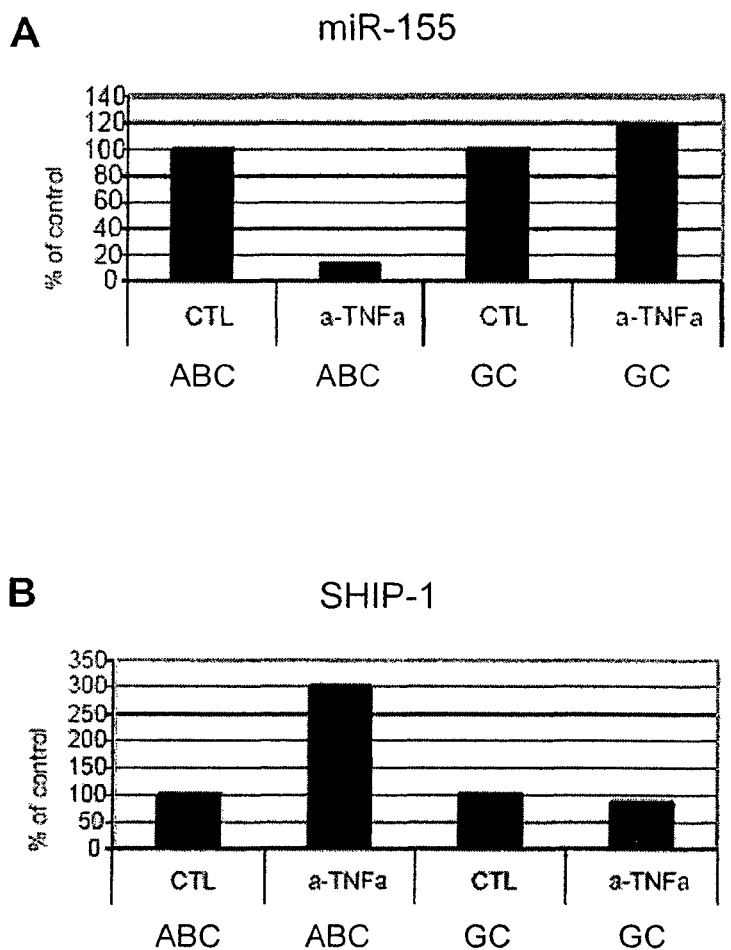
FIG. 8 shows that anti-TNF-alpha (infliximab) treatment of diffuse large B cell lymphoma (DLBCL) reduces expression of miR-155 and increases expression of SHIP1 in cells representing poor prognosis (ABC sub-type) DLBCL, but not in cells representing good prognosis (GC sub-type) DLBCL. Briefly, DLBCL cells were cultured in the presence or absence of 5 ng/ml anti-TNF alpha (infliximab) for eight hours. Afterwards the cells were harvested and washed in PBS before RNA was isolated using Trizol as directed by the manufacturer. Levels of miR-155 and SHIP1 mRNAs were determined by Q-PCR, normalized to U6B expression.

Toledo cells are a widely used cell line representative of ABC subtype DLBCL. Toledo cells were found to express higher miR-155, and consequently lower SHIP levels, when compared to Forage or Dohh2 cell lines representative of GC subtype DLBCL. Since B cells are known to produce TNFα, the possibility exists that DLBCL cells create an auto-stimulatory loop leading to elevated miR-155 levels by TNFα production. As described herein, Toledo cells were cultured in the presence of infliximab, a neutralizing humanized monoclonal antibody against TNFα (marketed as REMICADE by Centocor, Malvern, Pa.). Infliximab (U.S. Pat. No. 7,252,823 to Le et al., herein incorporated by reference) finds widespread clinical use in the treatment of inflammatory diseases such as rheumatoid arthritis and Crohn's disease. Strikingly anti-TNFα treatment of Toledo cells lead to a substantial reduction in miR-155 expression, with a concomitant increase in SHIP mRNA levels (FIG. 5). Toledo cells were also cultured in the presence of Eternacept, an antagonistic soluble TNFα receptor (co-marketed as ENBEL by Wyeth and Amgen). As was observed with infliximab treatment, eternacept treatment of Toledo cells lead to a remarkable increase in SHIP mRNA levels (FIG. 6). In addition, induction of SHIP expression in Toledo cells was accomplished by transfection with anti-miR-155.

Thus as determined during development of the present invention, miR-155 inhibits SHIP mRNA and protein expression. In addition, enhanced miR-155 expression in ABC-like DLBCL cells was found not to be a product of endogenous mutations, but rather the result of a TNFα-mediated autocrine feedback loop. Consequently, anti-TNFα regimens were found to be sufficient to reduce miR-155 levels, and restore expression of the tumor suppressor SHIP. By extension, downregulation of TNF alpha signaling in hematopoietic malignancies is contemplated to be an effective treatment when used alone or in conjunction with other treatment regimens.

IV. Therapeutic Formulations

Suitable TNFα inhibitors for use in the methods of the present invention to treat hematopoietic malignancies such as non-Hodgkin lymphoma include but are not limited to anti-TNFα antibodies and soluble TNFα receptors. Exemplary anti-TNFα antibodies include but are not limited to infliximab (marketed as REMICADE by Centocor) and adalimumab (marketed as HUMIRA by Abbott Laboratories). An exemplary Soluble TNFα receptor is the human immunoglobulin (IgG) fusion protein etanercept (co-marketed as ENBEL by Wyeth and Amgen). The treatment regimens of the present invention employing TNFα inhibitors may be used alone or in conjunction with other treatment regimens such as chemotherapy with CHOP, CHOP with rituximab, radiation, and/or surgery.

The antibodies and antibody fragments of some embodiments of the present invention may be administered by any suitable means, including parenteral, non-parenteral, subcutaneous, topical, intraperitoneal, intrapulmonary, intranasal, and intraregional administration (e.g., for local immunosuppressive treatment). Parenteral infusions include, but are not limited to, intramuscular, intravenous, intra-arterial, intraperitoneal, or subcutaneous administration. In addition, antibodies are suitably administered by pulse infusion, particularly with declining doses. Preferably, the dosing is given by injections, most preferably intravenous or subcutaneous injections, depending in part on whether the administration is brief or chronic.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. The dosages of the antibodies of the present invention are generally dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody fragment is 0.1-20 mg/kg, more preferably 1-10 mg/kg. In some embodiments, the dosage is from 50-600 mg/m$^2$ (e.g. 375 mg/m$^2$). It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the present invention.

The dosage administered will, of course, vary depending upon known factors such as the pharmacodynamic characteristics of the particular agent, its mode and route of administration, the age, health, and weight of the recipient, the nature and extent of symptoms, the kind of concurrent treatment, the frequency of treatment, and the effect desired. For example, a daily dosage of active ingredient can be about 0.01 to 100 milligrams per kilogram of body weight. Ordinarily 1 to 5, and preferably 1 to 10 milligrams per kilogram per day given in divided doses 1 to 6 times a day or in sustained release form, may be effective to obtain desired results.

As a non-limiting example, treatment can be provided as a daily dosage of anti-TNF-alpha peptides, monoclonal chimeric and/or murine antibodies of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4, or 2 hours, or any combination thereof.

In another example, treatment with infliximab (Remicade®) may be by intravenous administration at dosages less than 3 mg/kg (e.g., from 0.01 to 2.9 mg/kg), more than 5.7 mg/kg (e.g., from 5.8 to 500 mg/kg), on a daily basis for at least 2 days, and/or weekly basis for at least 2 weeks, monthly basis for at least two months, or any combination thereof.

In a further embodiment, treatment with etanercept (eternacept, Enbrel®) may be at a dosage less than 25 mg, more than 50 mg, on a daily basis for at least 2 days, and/or weekly basis for at least 2 weeks, monthly basis for at least two months, or any combination thereof.

In yet another embodiment, treatment with adalimumab (Humira®) may be by subcutaneous injection at dosages between 40 and 80 mg, less than 40 mg (e.g., from 0.1 to 39 mg) more than 80 mg (e.g., from 81 to 1000 mg) on a daily basis for at least 2 days, and/or weekly basis for at least 2 weeks, monthly basis for at least two months, or any combination thereof.

The antibody and antibody fragments of the invention can be incorporated into pharmaceutical compositions suitable for administration to a subject. For example, the pharmaceutical composition may comprise an antibody or antibody fragment and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of the following: water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibodies of the present invention.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody fragment) in the required amount in an appropriate solvent with one or a combination of ingredients enumerated above, as required, followed by sterile filtration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be achieved by including an agent that delays absorption (e.g., monostearate salts and gelatin).

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson. ed., Marcel Dekker, Inc., New York, 1978).

In certain embodiments, the binding molecules of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or antibody fragment of the invention.

A "therapeutically effective amount," "effective amount," "prophylactically effective amount," and "protective amount" of a composition with respect to a hematopoietic neoplasm interchangeably refer to, in one embodiment, an amount of the composition that delays, reduces, palliates, ameliorates, stabilizes, prevents and/or reverses one or more symptoms (e.g., clinical symptom, biochemical symptom, etc.) that are associated with the hematopoietic neoplasm compared to in the absence of the composition. This includes using dosages and periods of time necessary, to achieve the desired therapeutic result. The term "delaying" symptoms refers to increasing the time period between exposure to the immunogen or virus and the onset of one or more symptoms of the exposure. The term "eliminating" symptoms refers to 100% reduction of one or more symptoms of exposure to the immunogen or virus. A therapeutically effective amount also includes one in which any toxic or detrimental effects of the composition (e.g., antibody or antibody fragment) are outweighed by therapeutically beneficial effects. A "prophylactically effective amount" refers to an amount effective, at dosages and for periods of time necessary, to achieve the desired prophylactic result. In some embodiments, since a prophylactic dose is used in subjects prior to or at an earlier stage of disease, the prophylactically effective amount will be less than the therapeutically effective amount. Specific dosages can be readily determined by clinical trials and depend, for example, on the route of administration, disease state, age, sex, and weight of the individual (e.g. milligrams of drug per kg body weight). Dosages are further discussed below.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); C (degrees Centigrade); CHOP (cyclophosphamide/doxorubicin/vincristine/prednisone); IFN (interferon); TNF (tumor necrosis factor); DLBCL (diffuse large B-cell lymphoma); NHL (non-Hodgkin lymphoma); miR or miRNA (microRNA); PCR (polymerase chain reaction), QPCR (quantitative PCR).

Example 1

Treatment of Non-Hodgkin's Lymphoma

Patients with non-Hodgkin's lymphoma receive either a placebo and CHOP or one of several doses/schedules of a TNF-alpha inhibitor such as an anti-TNF-alpha antibody (e.g., infliximab marketed as REMICADE by Centocor) and cyclophosphamide, doxorubicin, vincristine, and prednisone (CHOP) chemotherapy. The CHOP chemotherapy regimen is as described in U.S. Pat. No. 5,736,137. Exemplary anti-TNF-alpha antibody doses/schedules are as follows: 3 mg/kg or 10 mg/kg by IV infusion at weeks 0, 2 and 6, followed by additional infusions every 4 or 8 weeks. After treatment, the patient is monitored to evaluate the effect on lymphoma status (e.g., number and size of tumors).

Example 2

Material and Methods

The following are exemplary materials and methods that were used to obtain data herein, including those described in Examples 3-5.
1. Cell Culture.
OCILY-3, OLILY-10 and Toledo cells were maintained in complete Iscove's DMEM+20% human serum+100 mg/ml penicillin/streptomycin+2 mM L-glutamine (Invitrogen). SUDHL-4 and Daudi cells were maintained in complete RPMI+10% FCS+100 mg/ml penicillin/streptomycin+2 mM L-glutamine. Cell proliferation was determined using a Coulter Counter.
2. Patient Samples
Frozen lymph node biopsies were stained with H&E, and lymphoma cells were isolated by laser-capture microdissection. All human material was handled in full compliance with NIH guidelines and IRB approval.
3. Transfection of miRs
OptiMem (Invitrogen) and Mirus transfection reagent (Mirus Bio/Fisher Scientific) were combined according to the manufacturer instructions, and miR mimics or anti-miRs (mimics from Dharmacon, Lafayette, Colo.; anti-miRs from Applied Biosystems, Foster City, Calif.) were introduced prior to addition of the transfection mix to the cells.
4. RNA Isolation and qPCR
RNA was extracted by TriZol, and qPCR was performed using primers targeting human SHIP (SuperArrays/SABiosciences, Frederick, Md.) and GAPDH (Dharmacon) for analysis of SHIP and GAPDH mRNA, miR-155, or U6 RNA by qPCR. Alternatively, miR kits (RT and TaqMan q-PCR primers, Applied Biosystems, Foster City, Calif.) were used for qPCR analysis of miR-155, U6 and U43 according to the manufactures instructions.
5. Western Blot Analysis
Cell lysates were subject to Western blot analysis using rabbit monoclonal antibodies against SHIP or GAPDH (Cell Signaling Tech, Danbars, Mass.), and blots were developed using ECL (GE Healthcare).

Example 3

Differential SHIP Expression Correlates with Prognosis of DLBCL

To determine whether a correlation exists between survival of patients with B cell malignancies and expression levels of PTEN and SHIP, we utilized ONCOMINE to query published cDNA array results. Analysis of data originating from gene expression studies by Alizadeh and Rosenwald (Alizadeh et al. (2000) Nature 403:503-511, Rosenwald et al. (2002) N Engl J Med 346:1937-1947), revealed that SHIP levels are significantly decreased in DLBCL compared to more indolent Chronic Lymphocytic Leukemia (CLL) or Follicular Lymphoma (FL) (FIG. 9A), moreover, SHIP levels were lower in non-GC (ABC)—compared to GC-DLBCL (not shown). Strikingly, SHIP levels within the non-GC subset displayed strong correlation with overall survival (FIG. 9B). These results suggest that SHIP expression levels are useful prognostic indicators of survival among DLBCL patients.

In order to determine the molecular mechanisms that mediate the observed decrease in SHIP expression in DLBCL, we determined the methylation status of the SHIP promoter in 44 non-GC and GC-DLBCL specimens, as well as screened for mutations in the coding regions and splice sequences, but did not detect any differences among the samples (not shown). We next considered the possibility that post-transcriptional regulatory events mediated by small non-coding RNAs might alter the expression of SHIP in these hematopoietic malignancies. Indeed, in addition to differential expression of coding genes, non-GC-type lymphoma cells express elevated levels of several microRNAs (miRs). Scanning of the SHIP 3' UTR revealed perfect sequence complementarity with the seed sequence of miR-155 (FIG. 9C), an onco-miR whose ectopic expression gives rise to B cell malignancies (Costinean et al. (2006) Proc Natl Acad Sci USA 103:7024-70298), but whose cellular targets have remained elusive.

Using a prototypic cell line model of the GC- and a non-GC-subtypes of DLBCL, Lawrie et al. (Lawrie et al. (2007) Int J Cancer 121:1156-1161) showed that in addition to miR-155, microRNAs miR-221 and miR-21 were also over-expressed in non-GC-type but not GC-type lymphoma cells. To determine miR-155 and SHIP-mRNA levels in primary DLBCL patient samples without concern of potential contamination by non-malignant tissue, we isolated tumor cells by Laser-Capture-Micro-Dissection from frozen lymph node biopsies. As shown in FIG. 9D, miR-155 expression was significantly higher in non-GC-DLBCL compared to GC-DLBCL, whereas SHIP mRNA levels were lower in non-GC-DLBCL, consistent with the notion of attenuation of SHIP expression by miR-155.

Example 4

Autocrine Stimulation of Non-GC DLBCL by TNFα

Figure 10:
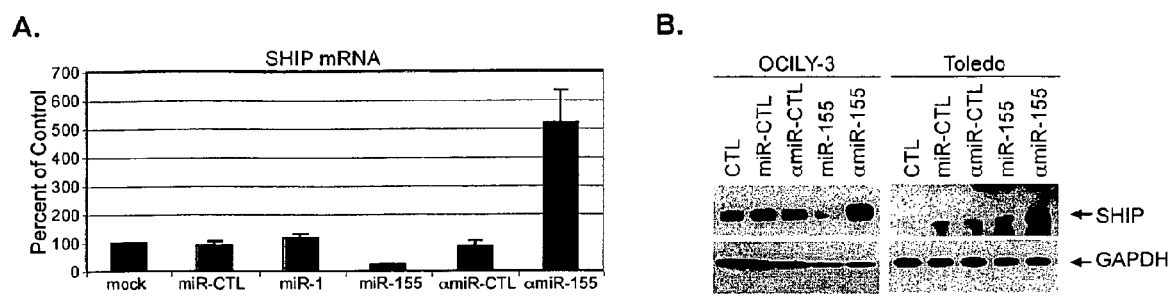
FIG. 10 shows that miR-155 attenuates SHIP expression. Non-GC-DLBCL cell lines OCILY-3 and Toledo were transfected with 50 μM of either non-specific miR (miR-CTL), miR-1, miR-155, non-specific anti-miR (αmiR-CTL) or anti-miR-155 (αmiR-1500). (A) Cells were harvested 12 hours post transfection, SHIP mRNA levels were determined by qPCR and normalized to GAPDH (mean+/−STD; n=4). (B) Same as (A), except cells were lysed after 72 hours, and Western blot analysis was performed using antibodies against human SHIP and GAPDH.

To establish a link between miR-155 and SHIP expression beyond mere correlation, the non-GC-DLBCL cell lines OCILY-3 was transfected either with a non-specific control-miR, miR-1, or miR-155. Neither miR-1 nor the control miR affected SHIP mRNA levels, whereas introduction of miR-155 resulted in a clear decrease in SHIP mRNA (FIG. 10A). More importantly, neutralization of endogenous miR-155 by means of a synthetic anti-miR resulted in a dramatic increase in SHIP mRNA compared to a transfection of a non-specific anti-miR control (FIG. 10A). As anticipated, the modulation of SHIP mRNA levels by miR-155 or anti-miR-155 is reflected by accompanying changes in SHIP protein expression (FIG. 10B, left panel), and is not unique to OCILY-3 cells, but is also observed in the Toledo cells, a widely used cell line model representative of non-GC-DLBCL (FIG. 10B, right panel).

Figure 11:
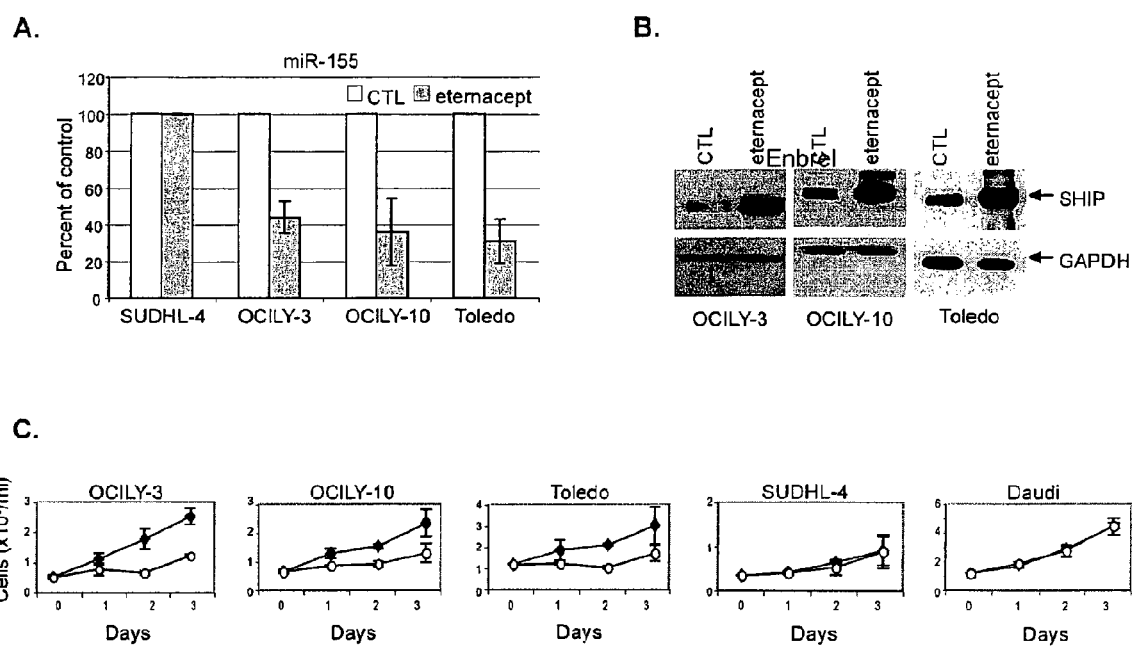
FIG. 11 shows autocrine stimulation of non-GC DLBCL by TNF-alpha. Non-GC-DLBCL cell lines OCILY-3, OCILY-10, Toledo, and the GC-DLBCL cell line SUDHL-4 and the Burkitt lymphoma Daudi were treated with 100 ng/ml eternacept as indicated. (A) miR-155 expression levels were determined by qPCR and normalized to U6 RNA (mean+/−STD; n=3); (B) Cells were harvested after 72 hrs, and SHIP protein expression was determined by Western blot analysis; (C) Cell proliferation was determined in triplicate cultures 24, 48, and 72 hours after addition of eternacept (mean+/−SD of at least three independent experiments).

The biological significance of these observations is evidenced by the finding that eternacept imposes significant antiproliferative effects upon the three non-GC-DLBCL cell lines, but did not produce any growth modulation in the GC-DLBCL cells, or in Daudi Burkitt lymphoma (FIG. 11C).

Example 5

Anti-TNFα Regimen Inhibits DLBCL Growth in vivo

Figure 12:
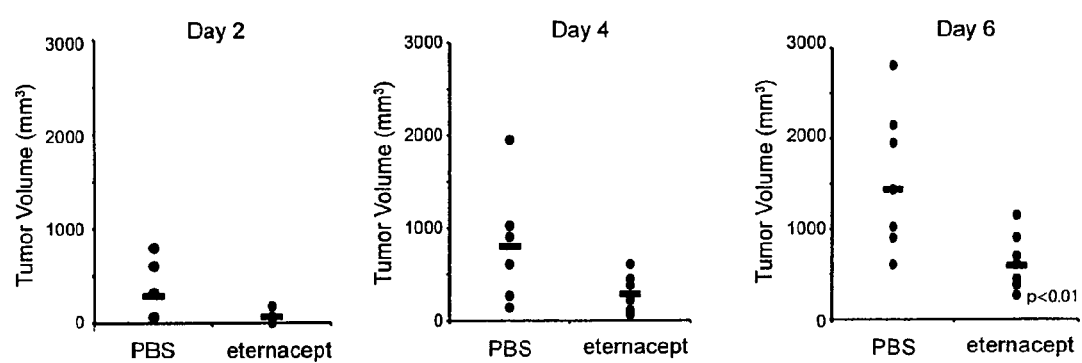
FIG. 12 shows anti-TNF-alpha regimen inhibits DLBCL growth in vivo. Sub-lethally irradiated (4 Gy) NOD/SCID mice were injected subcutaneously with 10⁷ non-GC-DL-BCL cells (Toledo). Upon establishment of palpable tumors, mice were injected every three days with 100 μg eternacept intravenously (i.v.), and tumor size was measured every second day with callipers.

The above data demonstrated that in non-GC-DLBCL, elevated levels of miR-155, and consequent abrogation of SHIP expression, are mediated through autocrine stimulation of cells by TNFα, a proinflammatory cytokine whose serum levels are known to be elevated in DLBCL patients (Pedersen et al. (2005) Br J Haematol 128:813-81913). To explore the potential efficacy of anti-TNFα regimen as a treatment for non-GC-DLBCL patients, we employed xenograft models in which Nod/SCID mice were subcutaneously inoculated with non-GC-DLBCL Toledo cells. Upon establishment of palpable tumors, the animals received either 100 μg eternacept or solvent intravenously every three days, and tumor size was measured after 2, 4 or 6 days. As shown in FIG. 12, eternacept treatment resulted in a slight, but detectable inhibition in tumor growth at day 4, and produced a substantial reduction in tumor burden after 6 days.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

We claim:

1. A method of treating non-Hodgkin diffuse large B-cell lymphoma (DLBCL) of an activated B-cell (ABC) subtype in a mammalian subject, comprising administering to the mammalian subject having an ABC-subtype DLBCL an effective amount of adalimumab that reduces expression of inositol polyphosphate-5-phosphatase (SHIP-1) and increases expression of miR-155 in said non-Hodgkin diffuse large B-cell lymphoma (DLBCL) of an activated B-cell (ABC) subtype.

2. A method of treating non-Hodgkin diffuse large B-cell lymphoma (DLBCL) in a human subject, comprising
   a) detecting increased expression of miR-155 and decreased expression of SHIP-1 in cells of said non-Hodgkin DLBCL in relation to their expression in germinal center B-cell (GCB) subtype DLBCL cells, and
   b) administering to the human subject an effective amount of adalimumab.

3. The method of claim 2, wherein said DLBCL is an activated B-cell (ABC) subtype DLBCL.

4. A method of treating an activated B-cell (ABC) subtype diffuse large B-cell lymphoma (DLBLC) in a mammalian subject, comprising administering adalimumab to a mammalian subject having ABC subtype DLBLC in an amount effective to reduce one or more symptoms of said ABC subtype DLBLC.

5. A method of treating an activated B-cell (ABC) subtype diffuse large B-cell lymphoma (DLBLC) in a mammalian subject, comprising
   a) obtaining ABC subtype DLBLC tumor cells from the human subject,
   b) detecting increased expression of miR-155 and decreased expression of SHIP-1 in said tumor cells obtained from the human subject in relation to the expression of miR-155 and SHIP-1 in germinal center B-cell (GBC) subtype DLBCL cells, and
   c) administering to the human subject having ABC subtype DLBLC tumor cells with increased expression of miR-155 and decreased expression of SHIP-1 adalimumab in an amount effective to reduce one or more symptoms of said ABC subtype DLBLC tumor cells.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
guguucggag gggugaaagc auuaa                                              25

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
uuaaugcuaa ucgugauagg gg                                                 22

<210> SEQ ID NO 3
<211> LENGTH: 22
<212> TYPE: DNA
<213> ORGANISM: Artificial Sequence

```
<220> FEATURE:
<223> OTHER INFORMATION: Synthetic

<400> SEQUENCE: 3
aguuguaguc agacuauucg au                                                  22

<210> SEQ ID NO 4
<211> LENGTH: 233
<212> TYPE: PRT
<213> ORGANISM: Homo sapiens

<400> SEQUENCE: 4

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
    195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 5
<211> LENGTH: 1669
<212> TYPE: DNA
<213> ORGANISM: Homo sapiens

<400> SEQUENCE: 5
ctccctcagc aaggacagca gaggaccagc taagagggag agaagcaact acagaccccc      60
cctgaaaaca accctcagac gccacatccc ctgacaagct gccaggcagg ttctcttcct    120
ctcacatact gacccacggc tccaccctct ctcccctgga aggacaccat gagcactga     180 aagcatgatc cgggacgtgg agctggccga ggaggcgctc cccaagaaga caggggggcc    240
ccagggctcc aggcggtgct tgttcctcag cctcttctcc ttcctgatcg tggcaggcgc    300
caccacgctc ttctgcctgc tgcactttgg agtgatcggc cccagaggg aagagttccc    360
```

```
caggga ccctc tctctaatca gccctctggc ccaggcagtc agatcatctt ctcgaacccc    420
gagtgacaag cctgtagccc atgttgtagc aaaccctcaa gctgaggggc agctccagtg     480
gctgaaccgc cgggccaatg ccctcctggc caatggcgtg gagctgagag ataaccagct     540
ggtggtgcca tcagagggcc tgtacctcat ctactcccag gtcctcttca agggccaagg     600
ctgcccctcc acccatgtgc tcctcaccca caccatcagc cgcatcgccg tctcctacca     660
gaccaaggtc aacctcctct ctgccatcaa gagcccctgc cagagggaga ccccagaggg     720
ggctgaggcc aagccctggt atgagcccat ctatctggga ggggtcttcc agctggagaa     780
gggtgaccga ctcagcgctg agatcaatcg gcccgactat ctcgactttg ccgagtctgg     840
gcaggtctac tttgggatca ttgccctgtg aggaggacga acatccaacc ttcccaaacg     900
cctcccctgc ccaatccct ttattacccc ctccttcaga cccctcaac ctcttctggc       960
tcaaaaagag aattgggggc ttagggtcgg aacccaagct tagaacttta agcaacaaga    1020
ccaccacttc gaaacctggg attcaggaat gtgtggcctg cacagtgaag tgctggcaac    1080
cactaagaat tcaaactggg gcctccagaa ctcactgggg cctacagctt tgatccctga    1140
catctggaat ctggagacca gggagccttt ggttctggcc agaatgctgc aggacttgag    1200
aagacctcac ctagaaattg acacaagtgg accttaggcc ttcctctctc cagatgtttc    1260
cagacttcct tgagacacgg agcccagccc tccccatgga gccagctccc tctatttatg    1320
tttgcacttg tgattattta ttatttattt attatttatt tatttacaga tgaatgtatt    1380
tatttgggag accggggtat cctgggggac ccaatgtagg agctgccttg gctcagacat    1440
gttttccgtg aaaacggagc tgaacaatag gctgttccca tgtagccccc tggcctctgt    1500
gccttctttt gattatgttt tttaaaatat ttatctgatt aagttgtcta acaatgctg     1560
atttggtgac caactgtcac tcattgctga gcctctgctc cccaggggag ttgtgtctgt    1620
aatcgcccta ctattcagtg gcgagaaata aagtttgctt agaaaagaa                1669
```

<210> SEQ ID NO 6
<211> LENGTH: 403
<212> TYPE: PRT
<213> ORGANISM: Homo sapiens

<400> SEQUENCE: 6

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140
```

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Tyr Val Tyr
            165                 170                 175

Tyr Tyr Ser Tyr Leu Leu Lys Asn His Leu Asp Tyr Arg Pro Val Ala
        180                 185                 190

Leu Leu Phe His Lys Met Met Phe Glu Thr Ile Pro Met Phe Ser Gly
            195                 200                 205

Gly Thr Cys Asn Pro Gln Phe Val Cys Gln Leu Lys Val Lys Ile
        210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Ile Asp Ser Ile Cys
290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
        355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu Asp Gln His Thr Gln Ile
385                 390                 395                 400

Thr Lys Val

<210> SEQ ID NO 7
<211> LENGTH: 5572
<212> TYPE: DNA
<213> ORGANISM: Homo sapiens

<400> SEQUENCE: 7
cctcccctcg cccggcgcgg tcccgtccgc ctctcgctcg cctcccgcct cccctcggtc      60
ttccgaggcg cccgggctcc cggcgcggcg gcggaggggg cggcaggcc ggcgggcggt     120 gatgtggcgg gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300
gcccctctca gcgcctgtga gcagccgcgg gggcagcgcc ctcggggagc cggccggcct     360
gcggcggcgc cagcggcggc gtttctcgcc tcctcttcgt cttttctaac cgtgcagcct     420
cttcctcggc ttctcctgaa agggaaggtg gaagccgtgg gctcgggcgg gagccggctg     480
aggcgcggcg gcggcggcgg cacctcccgc tcctggagcg gggggagaa gcggcggcg     540 cggcggccgc ggcggctgca gctccaggga gggggtctga gtcgcctgtc accatttcca     600

```
gggctgggaa cgccggagag ttggtctctc cccttctact gcctccaaca cggcggcggc    660
ggcggcggca catccaggga cccgggccgg ttttaaacct cccgtccgcc gccgccgcac    720
cccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
aagcggcggc agagcgaggg gcatcagcta ccgccaagtc cagagccatt ccatcctgc     960 agaagaagcc ccgccaccag cagcttctgc catctctctc ctccttttc ttcagccaca    1020 ggctcccaga catgacagcc atcatcaaag agatcgttag cagaaacaaa aggagatatc    1080
aagaggatgg attcgactta gacttgacct atatttatcc aaacattatt gctatgggat    1140
ttcctgcaga aagacttgaa ggcgtataca ggaacaatat tgatgatgta gtaaggtttt    1200
tggattcaaa gcataaaaac cattacaaga tatacaatct ttgtgctgaa agacattatg    1260
acaccgccaa atttaattgc agagttcac aatatccttt tgaagaccat aaccccaccac    1320 agctagaact tatcaaaccc ttttgtgaag atcttgacca atggctaagt gaagatgaca    1380
atcatgttgc agcaattcac tgtaaagctg gaaagggacg aactggtgta atgatatgtg    1440
catatttatt acatcggggc aaattttaa aggcacaaga ggccctagat ttctatgggg     1500
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
agatgatgtt tgaaactatt ccaatgttca gtggcggaac ttgcaatcct cagtttgtgg    1680
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaagt agaaaatgga agtctatgtg    1920
atcaagaaat cgatagcatt tgcagtatag agcgtgcaga taatgacaag gaatatctag    1980
tacttacttt aacaaaaaat gatcttgaca aagcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga accttttgat gaagatcagc    2220
atacacaaat tacaaaagtc tgaatttttt tttatcaaga gggataaaac accatgaaaa    2280
taaacttgaa taaactgaaa atggaccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaggt tgtgtagctg tgtcatgtat     2460
ataccttttt gtgtcaaaag gacatttaaa attcaattag gattaataaa gatggcactt    2520
tcccgtttta ttccagtttt ataaaaagtg gagacagact gatgtgtata cgtaggaatt    2580 ttttccttttt gtgttctgtc accaactgaa gtggctaaag agcttgtgtga tatactggtt    2640 cacatcctac ccctttgcac ttgtggcaac agataagttt gcagttggct aagagaggtt    2700
tccgaagggt tttgctacat tctaatgcat gtattcgggt tagggaatg gagggaatgc     2760 tcagaaagga aataatttta tgctggactc tggaccatat accatctcca gctatttaca    2820 cacaccttc tttagcatgc tacagttatt aatctggaca ttcgaggaat tggccgctgt     2880
cactgcttgt tgtttgcgca tttttttta agcatattg gtgctagaaa aggcagctaa     2940
aggaagtgaa tctgtattgg ggtacaggaa tgaaccttct gcaacatctt aagatccaca    3000
```

```
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataatacctg ctgtggatgc ttcatgtgct gcctgcaagc ttcttttttc    3300
tcattaaata taaaatattt tgtaatgctg cacagaaatt ttcaatttga gattctacag    3360
taagcgtttt ttttctttga agatttatga tgcacttatt caatagctgt cagccgttcc    3420 accctttga ccttacacat tctattacaa tgaattttgc agttttgcac attttttaaa    3480
tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgattttt cagtagaaat tgtcctacat gtgctttatt gatttgctat    3660
tgaaagaata gggttttttt ttttttttt tttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggttttt tttccagaaa tttggtgtct    3900
tcaaattata ccttcacctt gacatttgaa tatccagcca ttttgtttct taatggtata    3960
aaattccatt ttcaataact tattggtgct gaaattgttc actagctgtg gtctgaccta    4020
gttaatttac aaatacagat tgaataggac ctactagagc agcatttata gagtttgatg    4080
gcaaatagat taggcagaac ttcatctaaa atattcttag taaataatgt tgacacgttt    4140
tccatacctt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380 ttataaaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaactttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat acttttaaaa gggtagttga ataaatagca    4980
tcaccattct ttgctgtggc acaggttata aacttaagtg gagtttaccg gcagcatcaa    5040
atgtttcagc tttaaaaaat aaagtaggg tacaagttta atgtttagtt ctagaaattt    5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
```

```
gcctcttcag atactcttgt gctgtgcagc agtggctctg tgtgtaaatg ctatgcactg    5400
aggatacaca aaataccaa tatgatgtgt acaggataat gcctcatccc aatcagatgt     5460
ccatttgtta ttgtgtttgt taacaaccct ttatctctta gtgttataaa ctccacttaa    5520
aactgattaa agtctcattc ttgtcaaaaa aaaaaaaaaa aaaaaaaaaa aa            5572
```

```
<210> SEQ ID NO 8
<211> LENGTH: 1188
<212> TYPE: PRT
<213> ORGANISM: Homo sapiens

<400> SEQUENCE: 8

Met Val Pro Cys Trp Asn His Gly Asn Ile Thr Arg Ser Lys Ala Glu
1               5                   10                  15

Glu Leu Leu Ser Arg Thr Gly Lys Asp Gly Ser Phe Leu Val Arg Ala
            20                  25                  30

Ser Glu Ser Ile Ser Arg Ala Tyr Ala Leu Cys Val Leu Tyr Arg Asn
        35                  40                  45

Cys Val Tyr Thr Tyr Arg Ile Leu Pro Asn Glu Asp Asp Lys Phe Thr
    50                  55                  60

Val Gln Ala Ser Glu Gly Val Ser Met Arg Phe Phe Thr Lys Leu Asp
65                  70                  75                  80

Gln Leu Ile Glu Phe Tyr Lys Lys Glu Asn Met Gly Leu Val Thr His
                85                  90                  95

Leu Gln Tyr Pro Val Pro Leu Glu Glu Glu Asp Thr Gly Asp Asp Pro
            100                 105                 110

Glu Glu Asp Thr Glu Ser Val Val Ser Pro Pro Glu Leu Pro Pro Arg
        115                 120                 125

Asn Ile Pro Leu Thr Ala Ser Ser Cys Glu Ala Lys Glu Val Pro Phe
    130                 135                 140

Ser Asn Glu Asn Pro Arg Ala Thr Glu Thr Ser Arg Pro Ser Leu Ser
145                 150                 155                 160

Glu Thr Leu Phe Gln Arg Leu Gln Ser Met Asp Thr Ser Gly Leu Pro
                165                 170                 175

Glu Glu His Leu Lys Ala Ile Gln Asp Tyr Leu Ser Thr Gln Leu Ala
            180                 185                 190

Gln Asp Ser Glu Phe Val Lys Thr Gly Ser Ser Ser Leu Pro His Leu
        195                 200                 205

Lys Lys Leu Thr Thr Leu Leu Cys Lys Glu Leu Tyr Gly Glu Val Ile
    210                 215                 220

Arg Thr Leu Pro Ser Leu Glu Ser Leu Gln Arg Leu Phe Asp Gln Gln
225                 230                 235                 240

Leu Ser Pro Gly Leu Arg Pro Arg Pro Gln Val Pro Gly Glu Ala Asn
                245                 250                 255

Pro Ile Asn Met Val Ser Lys Leu Ser Gln Leu Thr Ser Leu Leu Ser
            260                 265                 270

Ser Ile Glu Asp Lys Val Lys Ala Leu Leu His Glu Gly Pro Glu Ser
        275                 280                 285

Pro His Arg Pro Ser Leu Ile Pro Pro Val Thr Phe Glu Val Lys Ala
    290                 295                 300

Glu Ser Leu Gly Ile Pro Gln Lys Met Gln Leu Lys Val Asp Val Glu
305                 310                 315                 320

Ser Gly Lys Leu Ile Ile Lys Ser Lys Asp Gly Ser Glu Asp Lys
                325                 330                 335
```

```
Phe Tyr Ser His Lys Lys Ile Leu Gln Leu Ile Lys Ser Gln Lys Phe
                340                 345                 350

Leu Asn Lys Leu Val Ile Leu Val Glu Thr Glu Lys Glu Lys Ile Leu
            355                 360                 365

Arg Lys Glu Tyr Val Phe Ala Asp Ser Lys Lys Arg Glu Gly Phe Cys
        370                 375                 380

Gln Leu Leu Gln Gln Met Lys Asn Lys His Ser Glu Gln Pro Glu Pro
385                 390                 395                 400

Asp Met Ile Thr Ile Phe Ile Gly Thr Trp Asn Met Gly Asn Ala Pro
                405                 410                 415

Pro Pro Lys Lys Ile Thr Ser Trp Phe Leu Ser Lys Gly Gln Gly Lys
            420                 425                 430

Thr Arg Asp Asp Ser Ala Asp Tyr Ile Pro His Asp Ile Tyr Val Ile
        435                 440                 445

Gly Thr Gln Glu Asp Pro Leu Ser Glu Lys Glu Trp Leu Glu Ile Leu
    450                 455                 460

Lys His Ser Leu Gln Glu Ile Thr Ser Val Thr Phe Lys Thr Val Ala
465                 470                 475                 480

Ile His Thr Leu Trp Asn Ile Arg Ile Val Val Leu Ala Lys Pro Glu
                485                 490                 495

His Glu Asn Arg Ile Ser His Ile Cys Thr Asp Asn Val Lys Thr Gly
            500                 505                 510

Ile Ala Asn Thr Leu Gly Asn Lys Gly Ala Val Gly Val Ser Phe Met
        515                 520                 525

Phe Asn Gly Thr Ser Leu Gly Phe Val Asn Ser His Leu Thr Ser Gly
    530                 535                 540

Ser Glu Lys Lys Leu Arg Arg Asn Gln Asn Tyr Met Asn Ile Leu Arg
545                 550                 555                 560

Phe Leu Ala Leu Gly Asp Lys Lys Leu Ser Pro Phe Asn Ile Thr His
                565                 570                 575

Arg Phe Thr His Leu Phe Trp Phe Gly Asp Leu Asn Tyr Arg Val Asp
            580                 585                 590

Leu Pro Thr Trp Glu Ala Glu Thr Ile Ile Gln Lys Ile Lys Gln Gln
        595                 600                 605

Gln Tyr Ala Asp Leu Leu Ser His Asp Gln Leu Leu Thr Glu Arg Arg
    610                 615                 620

Glu Gln Lys Val Phe Leu His Phe Glu Glu Glu Ile Thr Phe Ala
625                 630                 635                 640

Pro Thr Tyr Arg Phe Glu Arg Leu Thr Arg Asp Lys Tyr Ala Tyr Thr
                645                 650                 655

Lys Gln Lys Ala Thr Gly Met Lys Tyr Asn Leu Pro Ser Trp Cys Asp
            660                 665                 670

Arg Val Leu Trp Lys Ser Tyr Pro Leu Val His Val Cys Gln Ser
        675                 680                 685

Tyr Gly Ser Thr Ser Asp Ile Met Thr Ser Asp His Ser Pro Val Phe
    690                 695                 700

Ala Thr Phe Glu Ala Gly Val Thr Ser Gln Phe Val Ser Lys Asn Gly
705                 710                 715                 720

Pro Gly Thr Val Asp Ser Gln Gly Gln Ile Glu Phe Leu Arg Cys Tyr
                725                 730                 735

Ala Thr Leu Lys Thr Lys Ser Gln Thr Lys Phe Tyr Leu Glu Phe His
            740                 745                 750

Ser Ser Cys Leu Glu Ser Phe Val Lys Ser Gln Glu Gly Glu Asn Glu
```

-continued

|   |   |   |   |   |   |   |   |   |   |   |   |   |   |   |
|---|---|---|---|---|---|---|---|---|---|---|---|---|---|---|
|   |   |   | 755 |   |   |   | 760 |   |   |   | 765 |   |   |   |
| Glu | Gly | Ser | Glu | Gly | Glu | Leu | Val | Val | Lys | Phe | Gly | Glu | Thr | Leu | Pro |
| 770 |   |   |   |   | 775 |   |   |   |   | 780 |   |   |   |   |

Lys Leu Lys Pro Ile Ile Ser Asp Pro Glu Tyr Leu Leu Asp Gln His
785                790                 795                 800

Ile Leu Ile Ser Ile Lys Ser Ser Asp Ser Asp Glu Ser Tyr Gly Glu
                805                 810                 815

Gly Cys Ile Ala Leu Arg Leu Glu Ala Thr Glu Thr Gln Leu Pro Ile
            820                 825                 830

Tyr Thr Pro Leu Thr His His Gly Glu Leu Thr Gly His Phe Gln Gly
        835                 840                 845

Glu Ile Lys Leu Gln Thr Ser Gln Gly Lys Thr Arg Glu Lys Leu Tyr
850                 855                 860

Asp Phe Val Lys Thr Glu Arg Asp Glu Ser Ser Gly Pro Lys Thr Leu
865                 870                 875                 880

Lys Ser Leu Thr Ser His Asp Pro Met Lys Gln Trp Glu Val Thr Ser
                885                 890                 895

Arg Ala Pro Pro Cys Ser Gly Ser Ile Thr Glu Ile Ile Asn Pro
                900                 905                 910

Asn Tyr Met Gly Val Gly Pro Phe Gly Pro Pro Met Pro Leu His Val
            915                 920                 925

Lys Gln Thr Leu Ser Pro Asp Gln Gln Pro Thr Ala Trp Ser Tyr Asp
930                 935                 940

Gln Pro Pro Lys Asp Ser Pro Leu Gly Pro Cys Arg Gly Glu Ser Pro
945                 950                 955                 960

Pro Thr Pro Pro Gly Gln Pro Pro Ile Ser Pro Lys Lys Phe Leu Pro
                965                 970                 975

Ser Thr Ala Asn Arg Gly Leu Pro Pro Arg Thr Gln Glu Ser Arg Pro
            980                 985                 990

Ser Asp Leu Gly Lys Asn Ala Gly Asp Thr Leu Pro Gln Glu Asp Leu
        995                 1000                1005

Pro Leu Thr Lys Pro Glu Met Phe Glu Asn Pro Leu Tyr Gly Ser
    1010                1015                1020

Leu Ser Ser Phe Pro Lys Pro Ala Pro Arg Lys Asp Gln Glu Ser
    1025                1030                1035

Pro Lys Met Pro Arg Lys Glu Pro Pro Pro Cys Pro Glu Pro Gly
    1040                1045                1050

Ile Leu Ser Pro Ser Ile Val Leu Thr Lys Ala Gln Glu Ala Asp
    1055                1060                1065

Arg Gly Glu Gly Pro Gly Lys Gln Val Pro Ala Pro Arg Leu Arg
    1070                1075                1080

Ser Phe Thr Cys Ser Ser Ser Ala Glu Gly Arg Ala Ala Gly Gly
    1085                1090                1095

Asp Lys Ser Gln Gly Lys Pro Lys Thr Pro Val Ser Ser Gln Ala
    1100                1105                1110

Pro Val Pro Ala Lys Arg Pro Ile Lys Pro Ser Arg Ser Glu Ile
    1115                1120                1125

Asn Gln Gln Thr Pro Pro Thr Pro Thr Pro Arg Pro Pro Leu Pro
    1130                1135                1140

Val Lys Ser Pro Ala Val Leu His Leu Gln His Ser Lys Gly Arg
    1145                1150                1155

Asp Tyr Arg Asp Asn Thr Glu Leu Pro His His Gly Lys His Arg
    1160                1165                1170

```
Pro Glu  Glu Gly Pro Pro Gly  Pro Leu Gly Arg Thr  Ala Met Gln
    1175             1180              1185
```

<210> SEQ ID NO 9
<211> LENGTH: 3667
<212> TYPE: DNA
<213> ORGANISM: Homo sapiens

<400> SEQUENCE: 9

```
tcggtggtgt gtgggtcctg ggggtgcctg ccggcccggc cgaggaggcc cacgcccacc      60
atggtcccct gctggaacca tggcaacatc acccgctcca aggcggagga gctgctttcc     120
aggacaggca aggacgggag cttcctcgtg cgtgccagcg agtccatctc ccgggcatac     180
gcgctctgcg tgctgtatcg gaattgcgtt tacacttaca gaattctgcc caatgaagat     240
gataaattca ctgttcaggc atccgaaggc gtctccatga ggttcttcac caagctggac     300
cagctcatcg agttttacaa gaaggaaaac atggggctgg tgacccatct gcaatacccT     360
gtgccgctgg aggaagagga cacaggcgac gaccctgagg aggacacaga aagtgtcgtg     420
tctccacccg agctgccccc aagaaacatc ccgctgactg ccagctcctg tgaggccaag     480
gaggttcctt tttcaaacga gaatcccga gcgaccgaga ccagccggcc gagcctctcc     540
gagacattgt tccagcgact gcaaagcatg gacaccagtg gcttccaga gagcatctt     600
aaggccatcc aagattattt aagcactcag ctcgcccagg actctgaatt tgtgaagaca     660
gggtccagca gtcttcctca cctgaagaaa ctgaccacac tgctctgcaa ggagctctat     720
ggagaagtca tccggaccct cccatccctg gagtctctgc agaggttatt tgaccagcag     780
ctctcccggg gcctccgtcc acgtcctcag gttcctggtg aggccaatcc catcaacatg     840
gtgtccaagc tcagccaact gacaagcctg ttgtcgtcca ttgaagacaa ggtcaaggcc     900
ttgctgcacg agggtcctga gtctccgcac cggccctccc ttatccctcc agtcaccttt     960
gaggtgaagg cagagtctct ggggattcct cagaaaatgc agctcaaagt cgacgttgag    1020
tctgggaaac tgatcattaa gaagtccaag gatggttctg aggacaagtt ctacagccac    1080
aagaaaatcc tgcagctgat taagtcacag aaatttctga ataagttggt gatcttggtg    1140
gaaacagaga aggagaagat cctgcggaag gaatatgttt ttgctgactc caaaaagaga    1200
gaaggcttct gccagctcct gcagcagatg aagaacaagc actcagagca gccggagccc    1260
gacatgatca ccatcttcat cggcacctgg aacatgggta acgccccccc tcccaagaag    1320
atcacgtcct ggtttctctc caaggggcag ggaaagacgc gggacgactc tgcggactac    1380
atcccccatg acatttacgt gatcggcacc caagaggacc cctgagtga aaggagtgg    1440
ctggagatcc tcaaacactc cctgcaagaa atcaccagtg tgacttttaa acagtcgcc    1500
atccacacgc tctggaacat ccgcatcgtg gtgctggcca agcctgagca cgagaaccgg    1560
atcagccaca tctgtactga caacgtgaag acaggcattg caaacacact ggggaacaag    1620
ggagccgtgg gggtgtcgtt catgttcaat ggaacctcct tagggttcgt caacagccac    1680
ttgacttcag gaagtgaaaa gaaactcagg cgaaaccaaa actatatgaa cattctccgg    1740
ttcctggccc tgggcgacaa gaagctgagt ccctttaaca tcactcaccg cttcacgcac    1800
ctcttctggt ttggggatct taactaccgt gtggatctgc ctacctggga ggcagaaacc    1860
atcatccaga aaatcaagca gcagcagtac gcagacctcc tgtcccacga ccagctgctc    1920
acagagagga gggagcagaa ggtcttccta cacttcgagg aggaagaaat cacgtttgcc    1980
ccaacctacc gttttgagag actgactcgg gacaaatacg cctacaccaa gcagaaagcg    2040
```

```
acagggatga agtacaactt gccttcctgg tgtgaccgag tcctctggaa gtcttatccc    2100
ctggtgcacg tggtgtgtca gtcttatggc agtaccagcg acatcatgac gagtgaccac    2160
agccctgtct ttgccacatt tgaggcagga gtcacttccc agtttgtctc caagaacggt    2220
cccgggactg ttgacagcca aggacagatt gagtttctca ggtgctatgc acattgaag    2280 accaagtccc agaccaaatt ctacctggag ttccactcga gctgcttgga gagttttgtc    2340
aagagtcagg aaggagaaaa tgaagaagga agtgaggggg agctggtggt gaagtttggt    2400
gagactcttc caaagctgaa gcccattatc tctgaccctg agtacctgct agaccagcac    2460
atcctcatca gcatcaagtc ctctgacagc gacgaatcct atggcgaggg ctgcattgcc    2520
cttcggttag aggccacaga aacgcagctg cccatctaca cgcctctcac ccaccatggg    2580
gagttgacag gccacttcca gggggagatc aagctgcaga cctctcaggg caagacgagg    2640
gagaagctct atgactttgt gaagacggag cgtgatgaat ccagtgggcc aaagaccctg    2700
aagagcctca ccagccacga ccccatgaag cagtgggaag tcactagcag ggcccctccg    2760
tgcagtggct ccagcatcac tgaaatcatc aaccccaact acatgggagt ggggcccttt    2820
gggccaccaa tgcccctgca cgtgaagcag accttgtccc ctgaccagca gcccacagcc    2880
tggagctacg accagccgcc caaggactcc ccgctggggc cctgcagggg agaaagtcct    2940
ccgacacctc ccggccagcc gcccatatca cccaagaagt ttttaccctc aacagcaaac    3000
cggggtctcc ctcccaggac acaggagtca aggcccagtg acctggggaa gaacgcaggg    3060
gacacgctgc ctcaggagga cctgccgctg acgaagcccg agatgtttga gaaccccctg    3120
tatgggtccc tgagttcctt ccctaagcct gctcccagga aggaccagga atcccccaaa    3180
atgccgcgga aggaacccccc gccctgcccg gaacccggca tcttgtcgcc cagcatcgtg    3240
ctcaccaaag cccaggaggc tgatcgcggc gaggggcccg gcaagcaggt gcccgcgccc    3300
cggctgcgct ccttcacgtg ctcatcctct gccgagggca gggcggccgg cggggacaag    3360
agccaaggga agcccaagac cccggtcagc tcccaggccc cggtgccggc caagaggccc    3420
atcaagcctt ccagatcgga aatcaaccag cagaccccgc ccaccccgac gccgcggccg    3480
ccgctgccag tcaagagccc ggcggtgctg cacctccagc actccaaggg ccgcgactac    3540
cgcgacaaca ccgagctccc gcatcacggc aagcaccggc cggaggaggg gccaccaggg    3600
cctctaggca ggactgccat gcagtgaagc cctcagtgag ctgccactga gtcgggagcc    3660
cagagga                                                              3667
```

<210> SEQ ID NO 10
<211> LENGTH: 297
<212> TYPE: PRT
<213> ORGANISM: Artificial Sequence
<220> FEATURE:
<223> OTHER INFORMATION: Synthetic
<400> SEQUENCE: 10

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60
```

| | | | | | | | | | | | | |
|---|---|---|---|---|---|---|---|---|---|---|---|---|
|Ala|Leu|Gly|Gly|Leu|Leu|Met|Ile|Pro|Ala|Gly|Ile|Tyr|Ala|Pro|Ile|
|65| | | | |70| | | |75| | | |80|

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 11
<211> LENGTH: 934
<212> TYPE: DNA
<213> ORGANISM: Artificial Sequence
<220> FEATURE:
<223> OTHER INFORMATION: Synthetic

<400> SEQUENCE: 11
gtacaaaaaa gcaggctcca ccatgacaac acccagaaat tcagtaaatg ggactttccc   60
ggcagagcca atgaaaggcc ctattgctat gcaatctggt ccaaaaccac tcttcaggag  120
gatgtcttca ctggtgggcc ccacgcaaag cttcttcatg agggaatcta agactttggg  180
ggctgtccag attatgaatg ggctcttcca cattgccctg gggggtcttc tgatgatccc  240
agcagggatc tatgcaccca tctgtgtgac tgtgtggtac cctctctggg gaggcattat  300
gtatattatt tccggatcac tcctggcagc aacggagaaa aactccagga agtgtttggt  360
caaaggaaaa atgataatga attcattgag cctctttgct gccatttctg gaatgattct  420
ttcaatcatg gacatactta atattaaaat ttcccatttt ttaaaaatgg agagtctgaa  480
ttttattaga gctcacacac catatattaa catatacaac tgtgaaccag ctaatccctc  540
tgagaaaaac tccccatcta cccaatactg ttacagcata caatctctgt tcttgggcat  600
tttgtcagtg atgctgatct ttgccttctt ccaggaactt gtaatagctg gcatcgttga  660
gaatgaatgg aaaagaacgt gctccagacc caaatctaac atagttctcc tgtcagcaga  720

-continued

```
agaaaaaaaa gaacagacta ttgaaataaa agaagaagtg gttgggctaa ctgaaacatc       780
ttcccaacca aagaatgaag aagacattga aattattcca atccaagaag aggaagaaga       840
agaaacagag acgaactttc cagaacctcc ccaagatcag gaatcctcac caatagaaaa       900
tgacagctct cctttggacc cagctttctt gtac                                   934
```